United States Patent
Yang et al.

(10) Patent No.: US 12,394,165 B2
(45) Date of Patent: Aug. 19, 2025

(54) VESSEL DISPLAYING METHOD, COMPUTER DEVICE AND READABLE STORAGE MEDIUM

(71) Applicant: SHANGHAI UNITED IMAGING HEALTHCARE CO., LTD., Shanghai (CN)

(72) Inventors: Feng Yang, Shanghai (CN); Chang Liu, Shanghai (CN); Zhong-Yi Zhao, Shanghai (CN); Xiao-Yong Ji, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 174 days.

(21) Appl. No.: 18/088,088

(22) Filed: Dec. 23, 2022

(65) Prior Publication Data
US 2023/0206576 A1 Jun. 29, 2023

(30) Foreign Application Priority Data

Dec. 23, 2021 (CN) .......................... 202111591503.7
Dec. 27, 2021 (CN) .......................... 202111614404.6

(51) Int. Cl.
*G06T 15/00* (2011.01)
*G06T 7/11* (2017.01)
(Continued)

(52) U.S. Cl.
CPC ................ *G06T 19/20* (2013.01); *G06T 7/11* (2017.01); *G06T 7/50* (2017.01); *G06T 7/73* (2017.01);
(Continued)

(58) Field of Classification Search
CPC .......... G06T 7/155; G06T 2207/20044; G06T 2207/30048; G06T 2207/30172;
(Continued)

(56) References Cited

U.S. PATENT DOCUMENTS

| | | | | |
|---|---|---|---|---|
| 6,546,271 B1 * | 4/2003 | Reisfeld | ................. | A61B 5/062 600/407 |
| 7,497,988 B2 * | 3/2009 | Thut | ........................ | F27D 3/14 266/239 |

(Continued)

FOREIGN PATENT DOCUMENTS

| | | |
|---|---|---|
| CN | 108269257 A | 7/2018 |
| CN | 108399647 A | 8/2018 |

(Continued)

OTHER PUBLICATIONS

Mistelbauer G, Varchola A, Bouzari H, Starinsky J, Kochl A, Schernthaner R, Fleischmann D, Groller ME, Sramek M. Centerline reformations of complex vascular structures. In2012 IEEE Pacific Visualization Symposium Feb. 28, 2012 (pp. 233-240). IEEE.*

(Continued)

*Primary Examiner* — Phu K Nguyen

(57) ABSTRACT

A vessel displaying method and device, a computer device, and readable storage medium. The method includes: acquiring vessel information of a detected object, the vessel information including a vessel segment center line and corresponding vessel segment data of each vessel segment; receiving an edit instruction; editing an initial target vessel segment center line based on the edit instruction, to obtain a final target vessel segment center line; constructing a final target vessel segment according to the final target vessel segment center line; and constructing a target vessel based on the final target vessel segment, and displaying the target vessel.

18 Claims, 10 Drawing Sheets

(51) Int. Cl.
- *G06T 7/50* (2017.01)
- *G06T 7/73* (2017.01)
- *G06T 19/20* (2011.01)
- *A61B 6/50* (2024.01)

(52) U.S. Cl.
CPC ..... *A61B 6/504* (2013.01); *G06T 2207/20021* (2013.01); *G06T 2207/30048* (2013.01); *G06T 2207/30101* (2013.01); *G06T 2210/41* (2013.01); *G06T 2219/2021* (2013.01)

(58) Field of Classification Search
CPC . G06T 2207/30101; G06T 2207/20021; G06T 2219/2021; G06T 7/12; G06T 7/73; G06T 19/20; G06T 7/11; G06T 7/50; G06T 2207/20101; G06T 2210/41; A61B 6/504; A61B 6/466; A61B 6/5217; A61B 6/032
USPC ........................................................ 345/418
See application file for complete search history.

(56) References Cited

U.S. PATENT DOCUMENTS

| | | | | |
|---|---|---|---|---|
| 9,984,456 B2 * | 5/2018 | Wei | .......................... | G16H 50/20 |
| 2004/0249270 A1 * | 12/2004 | Kondo | ...................... | G06T 7/12 |
| | | | | 382/128 |
| 2013/0066188 A1 * | 3/2013 | Taerum | ................. | G06T 7/0012 |
| | | | | 600/407 |
| 2017/0262733 A1 * | 9/2017 | Gulsun | ................ | G06V 10/454 |
| 2019/0336096 A1 * | 11/2019 | Itu | ........................ | G16H 50/50 |
| 2020/0222018 A1 * | 7/2020 | van Walsum | .......... | A61B 6/463 |

FOREIGN PATENT DOCUMENTS

| | | |
|---|---|---|
| CN | 109448004 A | 3/2019 |
| CN | 113516700 A | 10/2021 |
| CN | 113616226 A | 11/2021 |

OTHER PUBLICATIONS

Kunio M, O'Brien CC, Lopes AC, Bailey L, Lemos PA, Tearney GJ, Edelman ER. Vessel centerline reconstruction from non-isocentric and non-orthogonal paired monoplane angiographic images. The international journal of cardiovascular imaging. May 2018;34:673-82.*

Chinese First Office Action (CN Application No. 202111591503.7), dated May 15, 2024, 7 pages.

Chinese First Office Action (CN Application No. 202111614404.6), dated May 1, 2024, 6 pages.

Sheng Huijuan et al., "Vessel centerline extraction based on minimum cost path algorithm", Computer Engineering and Applications, 2015, 51 (2) : 156-160, Jan. 15, 2015, (5 pages).

* cited by examiner

VESSEL DISPLAYING METHOD, COMPUTER DEVICE AND READABLE STORAGE MEDIUM

CROSS-REFERENCE TO RELATED APPLICATIONS

This application claims priority to Chinese patent application 202111591503.7, filed on Dec. 23, 2021 and entitled "METHOD AND DEVICE FOR EDITING VESSEL CENTER LINE, COMPUTER DEVICE, AND STORAGE MEDIUM", and Chinese patent application 202111614404.6, filed on Dec. 27, 2021 and entitled "VESSEL DISPLAYING METHOD AND DEVICE, COMPUTER DEVICE, AND STORAGE MEDIUM", the contents of which are hereby incorporated by reference in their entireties.

TECHNICAL FIELD

The present application relates to the field of medical technology, in particular to a vessel displaying method, a computer device, and a readable storage medium.

BACKGROUND

Surface rendering is widely used in a post-processing for medical images. Physicians may more intuitively observe shapes and relative positional relationship of internal tissues of an organ through a reconstructed three-dimensional model. A tubular network model, which has a more aesthetic, smooth and realistic display effect than conventional network models, is established for tubular structure tissues such as vessels and biliary tracts through a three-dimensional skeletonization.

In a conventional manner, during construction of a vessel, it is often required to perform frequent edit operations on vessel segment data to obtain a more complete and accurate segmentation result.

However, in relevant edit operations, each time after the vessel segment data are edited, the skeletonization processing for the vessel needs to be performed, that is, a vessel center line is generated, so that when the vessel is subsequently generated based on the vessel segment center line, the efficiency of generating the vessel is relatively low.

SUMMARY

Based on this, it is necessary to provide a vessel displaying method, a computer device, and a readable storage medium.

In a first aspect, the present disclosure provides a method for displaying a vessel, and the method includes: acquiring vessel information of a detected object, the vessel information including a vessel segment center line and corresponding vessel segment data of each vessel segment; receiving an edit instruction; editing an initial target vessel segment center line based on the edit instruction, to obtain a final target vessel segment center line; constructing a final target vessel segment according to the final target vessel segment center line; and constructing a target vessel based on the final target vessel segment, and displaying the target vessel.

In one of the embodiments, the receiving the edit instruction includes receiving a trim instruction, and the trim instruction includes to-be-trimmed region data.

The editing the initial target vessel segment center line based on the edit instruction to obtain the final target vessel segment center line, includes: determining an initial target vessel segment based on the trim instruction, and obtaining the initial target vessel segment center line of the initial target vessel segment; determining whether each initial center-line point of the initial target vessel segment center line is in the to-be-trimmed region data; and determining that the initial center-line point is a target center-line point corresponding to the trim instruction in response to the initial center-line point being in the to-be-trimmed region data, and deleting the target center-line point from the initial target vessel segment center line to obtain the final target vessel segment center line.

In one of the embodiments, the constructing the final target vessel segment according to the final target vessel segment center line includes: obtaining initial target vessel segment data corresponding to the initial target vessel segment; deleting initial vessel segment point data corresponding to the to-be-trimmed region data from the initial target vessel segment data to obtain final target vessel segment data; and constructing the final target vessel segment according to the final target vessel segment data and the final target vessel segment center line.

In one of the embodiments, the receiving the edit instruction includes receiving a modification instruction, and the modification instruction includes a vessel segment identification of an initial target vessel segment to be modified and to-be-modified region data.

The editing the initial target vessel segment center line based on the edit instruction to obtain the final target vessel segment center line includes: obtaining the initial target vessel segment center line of the initial target vessel segment to be modified according to the vessel segment identification; dividing the initial target vessel segment center line according to the to-be-modified region data, to obtain an initial first center line corresponding to the to-be-modified region data and a second center line without modification; and modifying a vessel name and/or the vessel segment identification of the initial first center line, to obtain a final first center line.

In one of the embodiments, the constructing the final target vessel segment according to the final target vessel segment center line includes: obtaining initial target vessel segment data of the initial target vessel segment to be modified according to the vessel segment identification; extracting vessel segment point data corresponding to the to-be-modified region data from the initial target vessel segment data, to obtain initial first vessel segment data to be modified; deleting the initial first vessel segment data from the initial target vessel segment data, to obtain second vessel segment data without modification; modifying the vessel name and/or the vessel segment identification in the initial first vessel segment data, to obtain final first vessel segment data; and constructing a final first target vessel segment according to the final first center line and the final first vessel segment data, and constructing a second target vessel segment according to the second center line and the second vessel segment data.

In one of the embodiments, the receiving the edit instruction includes receiving an adding instruction, and the adding instruction includes to-be-added vessel segment data of a vessel segment to be added and a vessel segment identification of an initial target vessel segment.

The editing the initial target vessel segment center line based on the edit instruction to obtain the final target vessel segment center line includes: obtaining an initial target vessel segment center line and initial target vessel segment data of the initial target vessel segment according to the vessel segment identification of the initial target vessel segment; generating combined vessel segment data based on the to-be-added vessel segment data and the initial target vessel segment data; determining a corresponding combined vessel segment center line according to the combined vessel segment data; and generating the final target vessel segment center line based on the initial target vessel segment center line and the combined vessel segment center line.

In one of the embodiments, the acquiring the vessel information of the detected object includes: acquiring scanned data of the detected object; dividing the scanned data to obtain original vessel information corresponding to the detected object; performing a thinning and skeletonization processing on the vessel information, to obtain the vessel segment center line corresponding to each vessel segment; and determining, based on each vessel segment center line, the vessel segment data of each vessel segment among the original vessel information.

In one of the embodiments, the method further includes: acquiring vessel segment center lines and corresponding vessel segment data of all non-target vessel segments; and constructing all the non-target vessel segments based on the vessel segment center lines and the corresponding vessel segment data of the non-target vessel segments.

In a second aspect, the present disclosure provides a vessel display device. The vessel display device includes a vessel information acquiring module, an edit instruction receiving module, a center line edit processing module, a vessel segment processing module, and a vessel constructing and displaying module.

The vessel information acquiring module is configured to acquire vessel information of a detected object, and the vessel information includes a vessel segment center line and vessel segment data of each vessel segment.

The edit instruction receiving module is configured to receive an edit instruction.

The center line edit processing module is configured to edit an initial target vessel segment center line based on the edit instruction, to obtain a final target vessel segment center line.

The vessel segment processing module is configured to construct a final target vessel segment according to the final target vessel segment center line.

The vessel constructing and displaying module is configured to construct a target vessel based on the final target vessel segment, and display target vessel.

In one of the embodiments, after the constructing the target vessel based on the final target vessel segment, and the displaying the target vessel, the method further includes: receiving a position adjusting instruction for a target vessel center line; obtaining a corresponding point on the target vessel center line according to the position adjusting instruction for the target vessel center line; extending a view ray in a current viewing-ray direction based on the corresponding point to obtain a front-surface intersection and a rear-surface intersection on the target vessel in the current viewing-ray direction, respectively; and determining depth information of the corresponding point according to the front-surface intersection and the rear-surface intersection.

In one of the embodiments, the extending the view ray in the current viewing-ray direction based on the corresponding point includes: acquiring the current viewing-ray direction of the corresponding point, and the front-surface intersection and the rear-surface intersection on the target vessel in the current viewing-ray direction; generating a unit vector according to the front-surface intersection and the rear-surface intersection; and extending the viewing ray along the unit vector direction sequentially by at least one unit vector length from the corresponding point.

In one of the embodiments, the method further includes: acquiring a previous center-line point of the corresponding point on the target vessel center line, when the viewing ray extended along the current viewing-ray direction based on the corresponding point does not contact a vessel tissue; and using depth information of the previous center-line point as the depth information of the corresponding point.

In one of the embodiments, the method further includes: acquiring a preset length when the viewing ray extended along the current viewing-ray direction based on the corresponding point contacts a non-vessel tissue first; acquiring a target point at which the current viewing ray intersects with the non-vessel tissue, and determining whether a length extended based on the target point along the current viewing-ray direction is less than the preset length; and continuing to extend the viewing ray in the current viewing-ray direction based on the target point in response to the length extended based on the target point in the current viewing-ray direction being less than the preset length, till the viewing ray contacts the vessel tissue to obtain the front-surface intersection and the rear-surface intersection on the target vessel, and calculating the depth information of the corresponding point according to the front-surface intersection and the rear-surface intersection.

In one of the embodiments, the method further includes: acquiring a previous center-line point of the corresponding point on the vessel center line in response to the length extended based on the target point in the current viewing-ray direction being greater than or equal to the preset length; and using the depth information of the previous center-line point as the depth information of the corresponding point.

In one of the embodiments, before the receiving the position adjusting instruction for the target vessel center line, the method further includes: receiving a selecting instruction for the target vessel center line through a target vessel image; and adjusting a viewing angle of a display of the target vessel image according to the target vessel center line selected based on the selecting instruction for the target vessel center line.

In one of the embodiments, the adjusting the viewing angle of the display of the target vessel image according to the target vessel center line selected based on the selecting instruction for the target vessel center line, includes: computing a target position of the target vessel image, a first feature point of the target vessel, and a second feature point of a branch to which the selected target vessel center line belongs; calculating a viewing ray vector based on the first feature point of the target vessel and the second feature point of the branch to which the selected target vessel center line belongs; simulating a rotation of the target vessel image at the target position of the target vessel image, and acquiring a rotation angle when the viewing ray vector is perpendicular to a screen inward; and adjusting the viewing angle of the display of the target vessel image based on the rotation angle.

In one of the embodiments, after the obtaining the corresponding point on the target vessel center line according to the position adjusting instruction for the target vessel center line, the method further includes adjusting trajectory information of the corresponding point.

In one of the embodiments, after the determining the depth information of the corresponding point according to the front-surface intersection and the rear-surface intersection, the method further includes adjusting the depth information of the corresponding point.

In an embodiment of the present disclosure, the vessel display device of the present application further includes a vessel center line position adjustment device. The vessel center line position adjustment device includes a position adjusting instruction receiving module, a trajectory information adjusting module, an intersection acquiring module, and a depth information adjusting module.

The position adjusting instruction receiving module is configured to receive a position adjusting instruction for a target vessel center line.

The trajectory information adjusting module is configured to obtain a corresponding point on the target vessel center line according to the position adjusting instruction for the target vessel center line.

The intersection acquiring module is configured to extend a view ray in a current viewing-ray direction based on the corresponding point to obtain a front-surface intersection and a rear-surface intersection on the target vessel in the current viewing-ray direction, respectively.

The depth information adjusting module is configured to determine depth information of the corresponding point according to the front-surface intersection and the rear-surface intersection.

In a third aspect, the present application also provides a computer device, including a memory and a processor. The memory has a computer program stored thereon, and the processor, when executing the computer program, performs steps of any one of the embodiments of the method above.

In a fourth aspect, the present application further provides non-transitory computer readable storage medium, having a computer program stored thereon. The computer program, when executed by a processor, performs steps of any one of the embodiments of the method above.

In a fifth aspect, the present application further provides a computer program product, including a computer program. The computer program, when executed by a processor, performs steps of any one of the embodiments of the method above.

In the vessel displaying method and device, the computer device and the non-transitory readable storage medium, the target vessel segment information of the detected object is acquired. The target vessel segment information includes the vessel segment center line and the corresponding vessel segment data of each target vessel segment. Then the edit instruction is received. The initial target vessel segment center line is edited based on the edit instruction, to obtain the final target vessel segment center line. Further, the final target vessel segment is constructed according to the final target vessel segment center line. The target vessel is constructed based on the final target vessel segment, and displayed. Therefore, each time the vessel is edited, the initial vessel segment center line may be edited according to the edit instruction, to generate the final target vessel segment center line, and the target vessel is constructed according to the edited final target vessel segment center line and is displayed. Compared with the conventional method for editing the vessel segment data, the solutions of the present application may reduce the number of skeletonization processings in an editing process, save the time for processing data, reduce the time of constructing the vessel, and further improve the efficiency of constructing and displaying the vessel.

In the position adjustment for the vessel center line, after the position adjusting instruction for the target vessel center line is received, the corresponding point is first determined, and the trajectory information is adjusted, and then the front-surface intersection and the rear-surface intersection of the target vessel in the current viewing-ray direction are obtained based on the current viewing-ray direction, so that the depth information may be obtained based on the front-surface intersection and the rear-surface intersection, thereby automatically determining the depth of the center-line point at the adjusted position, ensuring that the point is in the center of the vessel, correcting the center line quickly, accurately and completely, and improving the convenience of the position adjustment for the center line.

DETAILED DESCRIPTION OF THE EMBODIMENTS

In order to make the objectives, technical solutions and advantages of the present application clearer and to be better understood, the present application will be further described in detail hereinafter combining with the accompanying drawings and embodiments. It should be understood that the specific embodiments described hereinafter are only used to illustrate the present application, but not intended to limit the present application.

Figure 1:
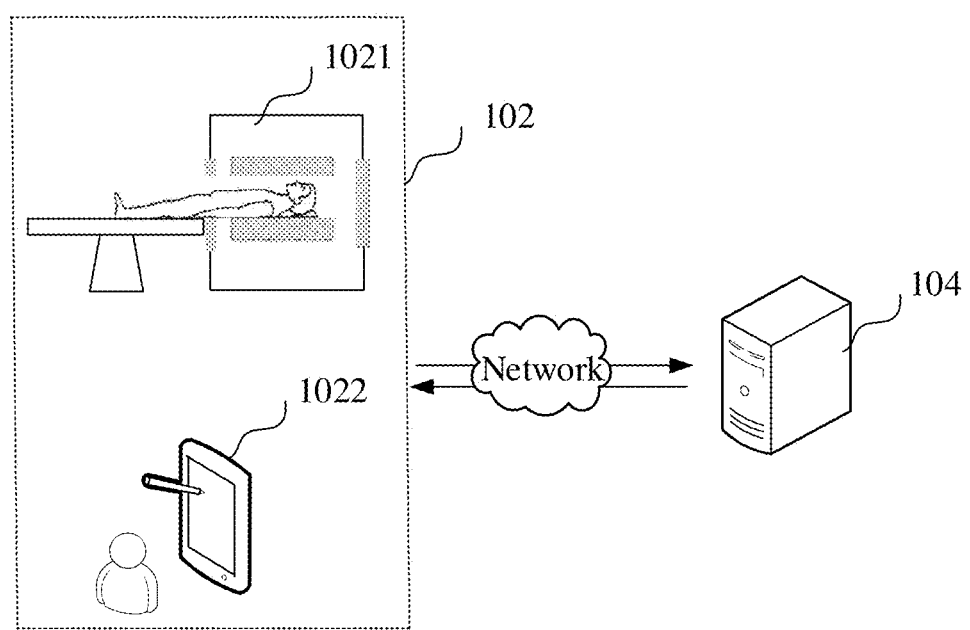
FIG. 1 is an application scene view of a vessel displaying method according to an embodiment of the present disclosure.

A vessel displaying method provided in the present application may be applied to an application scene shown in FIG. 1. A terminal 102 communicates with a server 104 through a network. Specifically, a user may acquire scanned data of a detected object through an acquisition terminal 1021 and transmit the scanned data to the server 104, so that the server 104 may acquire vessel information of the detected object based on the scanned data. The vessel information includes a vessel segment center line and corresponding vessel segment data of each vessel segment. Then, the server 104 may receive an edit instruction sent by an editing terminal 1022, perform an edit processing on a vessel segment center line of an initial target vessel segment based on the edit instruction, obtain an edited final target vessel segment center line, and construct a corresponding final target vessel segment according to the edited final target vessel segment center line. Further, the server 104 may construct a corresponding final target vessel segment based on the processed final target vessel segment data and the edited final target vessel segment center line, and construct and display a target vessel based on the final target vessel segments. In one of the embodiments, the server 104 may display all vessel segments. The acquisition terminal 1021 may include, but is not limited to, any device capable of scanning the detected object. For example, the acquisition terminal 1021 may include, but is not limited to a CT terminal, a magnetic resonance terminal device, and the like. The editing terminal 1022 may include, but is not limited to, any one of various personal computers, notebook computers, smartphones, tablets, and portable wearable devices. The server 104 may be implemented by a separate server, or by a server cluster composed of multiple servers.

Figure 2:
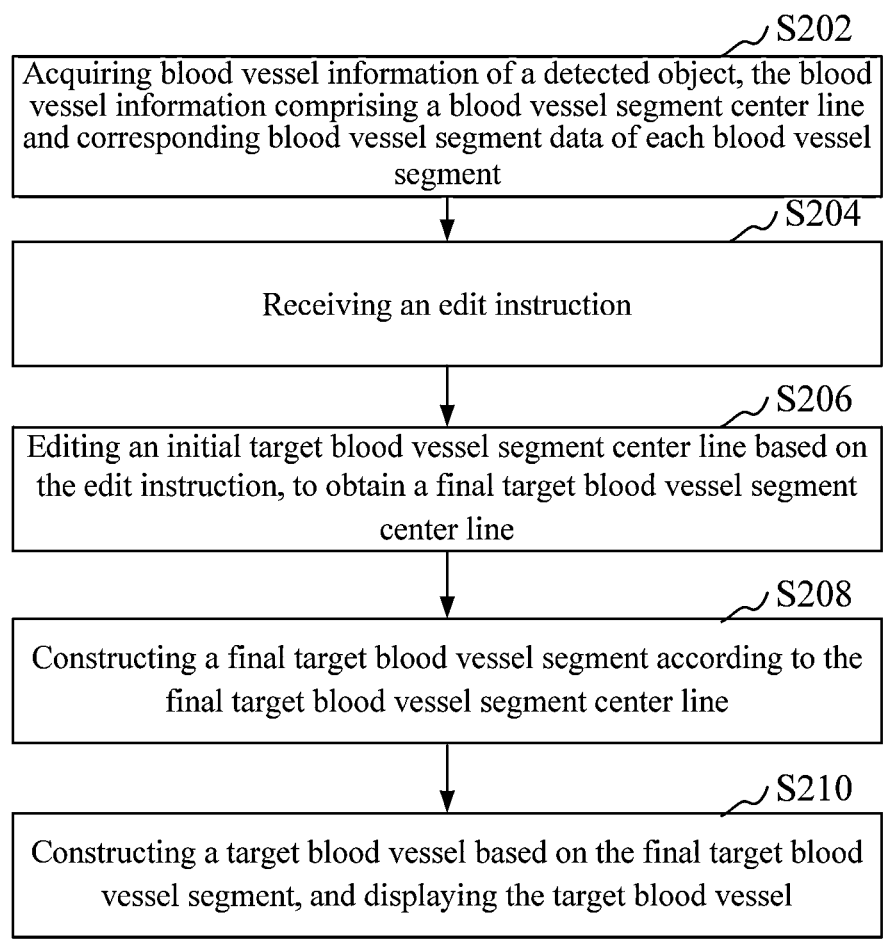
FIG. 2 is a schematic flowchart of the vessel displaying method according to an embodiment of the present disclosure.

In an embodiment, as shown in FIG. 2, a vessel displaying method is provided. By taking the method applied to the server in FIG. 1 for an example, the method includes the following steps S202 to S210.

In step S202, vessel information of a detected object is acquired, and the vessel information includes a vessel segment center line and vessel segment data of each vessel segment.

The detected object is the object that is detected in a medical test, and may be, for example, a patient, or a volunteer in a clinical trial.

In this embodiment, the vessel information refers to information of each vessel segment of the detected object, and may include for example, the vessel segment center line of each vessel segment, which may be referred to as a vessel skeleton line, and may further include the vessel segment data of each vessel segment, namely, data of all points constituting the vessel. For a computer, the vessel is composed of a series of points, and the vessel segment data include respective coordinate positions of points constituting the vessel segment. The vessel segment data may also be referred to as a three-dimensional vessel mask set.

It should be understood by those skilled in the art that, the vessel is a three-dimensional vessel, and the coordinate positions of each point in vessel segment data may include coordinates of three dimensions x, y, z. Similarly, the vessel segment center line may also include a plurality of points, and the position coordinates of each point may also be coordinates of three dimensions x, y, and z.

In this embodiment, the vessel information may include data of a plurality of vessel segments, and specifically may include a vessel segment center line set and a vessel segment data set. The vessel segment center line set includes vessel segment center lines of the plurality of vessel segments, and the vessel segment data set includes vessel segment data of the plurality of vessel segments.

In this embodiment, each vessel segment center line may include a corresponding vessel segment identification (denoted as Segment ID), a center line voxel set (i.e., points constituting the vessel segment center line and the respective coordinate positions of the points), and a radius r of the vessel. The vessel segment data of each vessel segment may include the corresponding vessel segment identification (denoted as Segment ID), and a vessel segment voxel set (i.e., points constituting vessel segment and the coordinate positions of the points).

In this embodiment, the server may scan the detected object through the scanning terminal, for example, through a CT scan or a magnetic resonance device scan, etc., to obtain the scanned data.

In this embodiment, after acquiring the vessel information of the detected object, the server may construct the corresponding vessel according to the vessel information, that is, construct a tubular network model of the corresponding vessel and send the tubular network model to the terminal to perform three-dimensional display through the terminal.

In step S204, an edit instruction is received.

The edit instruction refers to an editing operation performed on the vessel segments in the vessel information.

As described in the background, in order to obtain a more complete and accurate segmentation result of the vessel in an actual application, it is necessary to edit the vessel segment by frequent editing operations.

In this embodiment, the user may conduct an edit of the vessel presented by the terminal, to generate a corresponding edit instruction and send the corresponding edit instruction to the server, so that the server performs a subsequent processing after receiving the corresponding edit instruction.

In step S206, an initial target vessel segment center line is edited based on the edit instruction, to obtain a final target vessel segment center line.

In step S208, a final target vessel segment is constructed according to the final target vessel segment center line.

In this embodiment, after obtaining the edit instruction, the server may perform an edit processing on the vessel segment according to the edit instruction.

Specifically, the server determines a corresponding initial target vessel segment according to the edit instruction, and then performs the edit processing on the initial target vessel segment center line corresponding to the initial target vessel segment, to obtain the final target vessel segment center line.

Further, the server may perform the same processing on corresponding initial target vessel segment data according to the edited final target vessel segment center line, to obtain processed final target vessel segment data.

In this embodiment, the edit instruction may be the edit instruction simultaneously corresponding to a plurality of vessel segments, and the server may perform simultaneous multi-threading edit processings on the plurality of vessel segments.

In step S210, a target vessel is constructed based on the final target vessel segment, and displayed.

In this embodiment, after obtaining the processed final target vessel segment data and the edited final target vessel segment center line, the server may construct the final target vessel segment according to the method described above.

Based on the constructed final target vessel segment, the target vessel is constructed and sent to the terminal for a three-dimensional display.

Specifically, the method further includes: acquiring vessel segment center lines and corresponding vessel segment data of all non-target vessel segments; constructing all non-target vessel segments based on the vessel segment center lines and the corresponding vessel segment data of the non-target vessel segments.

In this embodiment, during construction of the vessel corresponding to the target vessel segment(s), all vessels of the detected object may be constructed, that is, the construction and display of the three-dimensional target vessels may be performed based on the non-target vessel segments and the edited final target vessel segment, so that an overall construction result of the vessels may be displayed through the terminal.

In the vessel displaying method above, the target vessel segment information of the detected object is acquired. The target vessel segment information includes the vessel segment center line and the corresponding vessel segment data of each target vessel segment. Then the edit instruction is received. The initial target vessel segment center line is edited based on the edit instruction, to obtain the final target vessel segment center line. Further, the final target vessel segment is constructed according to the final target vessel segment center line. The target vessel is constructed based on the final target vessel segment, and displayed. Therefore, each time the vessel is edited, the initial vessel segment center line may be edited according to the edit instruction, to generate the final target vessel segment center line, and the target vessel is constructed according to the edited final target vessel segment center line and is displayed. Compared with the conventional method for editing the vessel segment data, the solutions of the present application may reduce the number of skeletonization processings in an editing process, save the time of processing data, reduce the time of constructing the vessel, and further improve the efficiency of constructing and displaying the vessel.

In one of the embodiments, the vessel segment center line may include a first number of center-line points, and the vessel segment data may include a second number of vessel segment point data, and for the same vessel segment, there is a correspondence between each center-line point and at least one vessel segment point data.

As described above, each vessel segment center line may include the corresponding vessel segment identification, the center line voxel set, and the radius r of the vessel. The vessel segment data of each vessel segment may include a corresponding vessel segment identification and a vessel segment voxel set. That is, each vessel segment center line may include a plurality of center line voxels, i.e., the first number of the center-line points, and the vessel segment data of each vessel segment may include a plurality of vessel segment voxels, i.e., the second number of the vessel segment point data.

In an embodiment, for the same vessel segment, there is a corresponding relationship between each center-line point and at least one vessel segment point data. That is, for a certain center line voxel in the vessel segment center line, there may be, in the corresponding vessel segment data, at least one vessel segment voxel having a corresponding relationship with the certain center line voxel.

In the present embodiment, processing corresponding initial target vessel segment data according to the edited final target vessel segment center line, to obtain the processed final target vessel segment data, may include: processing the corresponding initial target vessel segment data according to the edited final target vessel segment center line and the corresponding relationship, to obtain the processed final target vessel segment data.

In this embodiment, after editing the initial target vessel segment center line based on the edit instruction, the server may process the initial vessel segment point data corresponding to the center-line points of the edited final vessel segment center line to obtain the processed final target vessel segment data, according to the corresponding relationship between the final vessel segment center-line point and the initial vessel segment point data.

It should be noted that the edit instruction above may include at least one of a trim instruction, a modification instruction and an adding instruction, and the edit instructions above will be described one by one hereinafter.

In one of the embodiments, receiving the edit instruction may include receiving the trim instruction. The trim instruction includes to-be-trimmed region data.

In one of the embodiments, the received edit instruction is the trim instruction, which includes the to-be-trimmed region data. The editing the initial target vessel segment center line based on the edit instruction to obtain the final target vessel segment center line, includes: determining the initial target vessel segment based on the trim instruction, and obtaining the initial target vessel segment center line of the initial target vessel segment; determining whether each initial center-line point of the initial target vessel segment center line is in the to-be-trimmed region data; and determining the initial center-line point is a target center-line point corresponding to the trim instruction when the initial center-line point is in the to-be-trimmed region data, and deleting the target center-line point from the initial target vessel segment center line to obtain the final target vessel segment center line.

In one of the embodiments, constructing the final target vessel segment according to final target vessel segment center line includes: obtaining the initial target vessel segment data corresponding to the initial target vessel segment; deleting initial vessel segment point data corresponding to the to-be-trimmed region data from the initial target vessel segment data to obtain the final target vessel segment data; constructing a corresponding final target vessel segment according to the final target vessel segment data and the final target vessel segment center line.

Specifically, the edit instruction may be the trim instruction, i.e., part of the vessel is trimmed during the edit for the vessel of the detected object.

In this embodiment, the trim instruction may include the to-be-trimmed region data of the corresponding region to be trimmed. The to-be-trimmed region data may have the same data type as the vessel segment data, i.e., may be a mask set.

In the present embodiment, the corresponding initial target vessel segment is determined based on the trim instruction, and the initial target vessel segment center line of the initial target vessel segment and the corresponding initial target vessel segment data are acquired. It is determined whether each initial center-line point of the initial target vessel segment center line is in the to-be-trimmed region data. It is determined that the initial center-line point is the target center-line point corresponding to the trim instruction, when the initial center-line point is in the to-be-trimmed region data, and the target center-line point is deleted from the initial target vessel segment center line to obtain the final target vessel segment center line. The vessel segment point data corresponding to the target center-line point is deleted from the initial target vessel segment data to obtain the final target vessel segment data.

In this embodiment, after receiving the trim instruction, the server may mark the to-be-trimmed region data carried in the trim instruction as mask1, then traverse the vessel segment center line set, and delete the target vessel center-line point corresponding to the to-be-trimmed region data mask1.

Further, the server may delete the initial target vessel segment data, which are corresponding to the initial target vessel segment center-line point of the target vessel to be trimmed, from the vessel segment data set.

In this embodiment, after determining the initial target vessel segment center line, the server may acquire each initial center line voxel in the initial target vessel segment center line, namely, each initial center-line point, and determine whether each initial center-line point in the initial target vessel segment center line is in the to-be-trimmed region data mask1.

In this embodiment, when the server determines that the initial center-line point is in the to-be-trimmed region data mask1, it is determined that the initial center-line point is the target center-line point corresponding to the trim instruction, and the target center-line point is deleted from the initial target vessel segment center line. When it is determined that the initial center-line point is not in the to-be-trimmed region data mask1, the server does not process the initial center-line point.

In this embodiment, the server may traverse all initial center-line points on the initial target vessel segment center line, to obtain the final target vessel segment center line.

Further, the initial vessel segment point data corresponding to the deleted center-line point are deleted from the initial target vessel segment data, to obtain the final target vessel segment data. Alternatively, the server may compare each initial vessel segment point data in the initial target vessel segment data with the to-be-trimmed region data mask1, determine whether the initial vessel segment point data are in the to-be-trimmed region data mask1, and delete the initial vessel segment point data when the initial vessel segment point data are in the to-be-trimmed region data mask1, and retain the initial vessel segment point data when the initial vessel segment point data are not in the to-be-trimmed region data mask1.

In some embodiments, for one vessel, two vessel segments or one vessel segment may be obtained after trimming. The trimming may include at least one of the following cases: trimming an edge of the vessel segment, trimming a middle portion of the vessel segment and splicing the trimmed vessel segments together, and trimming a portion between two vessel segments.

In some embodiments, the edit instruction may be a modification instruction, which is a processing of modifying a vessel name and/or the vessel segment identification of an initial first center line.

In one of the embodiments, receiving the edit instruction may include receiving the modification instruction, and the modification instruction includes the vessel segment identification of the initial target vessel segment to be modified and the to-be-modified region data.

In one of the embodiments, editing an initial target vessel segment center line based on the edit instruction to obtain a final target vessel segment center line, includes: obtaining an initial target vessel segment center line of an initial target vessel segment to be modified according to the vessel segment identification; dividing the initial target vessel segment center line according to the to-be-modified region data, to obtain the initial first center line corresponding to the to-be-modified region data and a second center line without modification; and performing a processing of modifying the vessel name and/or the vessel segment identification of the initial first center line, to obtain a final first center line.

In one of the embodiments, constructing the final target vessel segment according to final target vessel segment center line includes: obtaining initial target vessel segment data of an initial target vessel segment to be modified according to the vessel segment identification; extracting vessel segment point data corresponding to the to-be-modified region data from the initial target vessel segment data, to obtain initial first vessel segment data to be modified; deleting the initial first vessel segment data from the initial target vessel segment data, to obtain second vessel segment data without modification; modifying the vessel name and/or the vessel segment identification in the initial first vessel segment data, to obtain final first vessel segment data; and constructing a final first target vessel segment according to the final first center line and the final first vessel segment data, and constructing a second target vessel segment according to the second center line and the second vessel segment data.

Specifically, the edit instruction may be the modification instruction, i.e., during the edit for the vessel segment of the detected object, one or more vessels are modified to be another vessel, e.g., a portal vessel is modified to be a venous vessel, or a portion of one vessel is modified to be a portion of another vessel, etc.

In some embodiments, the modification instruction may include the to-be-modified region data, and the vessel segment identification of the initial target vessel segment to be modified, such as the Segment ID described above.

In some embodiments, the initial target vessel segment center line and the initial target vessel segment data of the initial target vessel segment to be modified are acquired according to the vessel segment identification. The initial target vessel segment center lines are divided according to the to-be-modified region data, to obtain an initial first center line corresponding to the to-be-modified region data and the second center line without modification. Among the initial target vessel segment data, the initial first vessel segment data corresponding to the initial first center line and the second vessel segment data corresponding to the second center line are determined based on the initial first center line and the second center line. According to the to-be-modified region data, the initial first center line and the initial first vessel segment data are modified to obtain the modified final first center line and the final first vessel segment data. Specifically, the vessel name and/or the vessel segment identification of the initial first center line are modified, to obtain the modified final first center line.

In this embodiment, after receiving the modification instruction, the server may acquire, from the vessel segment center line set, the initial target vessel segment center line of the initial target vessel segment to be modified, according to the vessel segment identification, and acquire the corresponding initial target vessel segment data from the vessel segment data set.

Alternatively, the server may mark the to-be-modified region data carried in the modification instruction as mask2, then traverse the vessel segment center line set, take out the initial target vessel segment center line of the initial target vessel segment corresponding to the to-be-modified region data mask2, and store it in a new vessel segment center line set.

Further, the server divides initial target vessel segment center lines according to the to-be-modified region data mask2, to obtain the initial first center line corresponding to the to-be-modified region data mask2 and the second center line without modification.

Specifically, the server may determine whether each center-line point on the initial target vessel segment center line is in the to-be-modified region data mask2. When a center-line point is in the to-be-modified region data mask2, the server stores the center-line point into a new initial first center line. When the center-line point is not in the to-be-modified region data mask2, the server stores the center-line point into a new second center line. The server may generate a corresponding initial first center line and the second center line by traversing each center-line point in the target vessel segment center line.

It should be understood by those skilled in the art that in some special cases, the initial first center line or the second center line may not exist. For example, when center-line points on the initial target vessel segment center line are all in the to-be-modified region data mask2, second center line does not exist, and when no center-line point on the initial target vessel segment center line is in the to-be-modified region data mask2, the initial first center line does not exist.

In this embodiment, the server may determine, among the initial target vessel segment data, the initial first vessel segment data corresponding to the initial first center line and the second vessel segment data corresponding to the second center line. That is, the server may divide the initial target vessel segment data corresponding to the initial target vessel segment center line into the initial first vessel segment data corresponding to the initial first center line and the second vessel segment data corresponding to the second center line.

Further, the server may modify the initial first center line and the initial first vessel segment data according to the to-be-modified region data, e.g., modify the vessel segment identification or the vessel type, etc., to obtain a final first center line and the final first vessel segment data.

In one of the embodiments, the server may also determine, among the initial target vessel segment data, the initial first vessel segment data corresponding to the initial first center line and the second vessel segment data corresponding to the second center line, according to the to-be-modified region data mask2. That is, the server may traverse each initial target vessel segment point data, determine whether each initial target vessel segment point data is in the to-be-modified region data mask2; if an initial target vessel segment point data is in the to-be-modified region data mask2, it is determined that the initial target vessel segment point data are the initial first vessel segment data corresponding to the initial first center line; and if an initial target vessel segment point data are not in the to-be-modified region data mask2, it is determined that the initial vessel segment point data are the second vessel segment data corresponding to the second center line.

In one of the embodiments, receiving the edit instruction may include receiving an adding instruction. The adding instruction includes to-be-added vessel segment data of a to-be-added vessel segment, and the vessel segment identification of the initial target vessel segment. The adding instruction instructs to add the to-be-added vessel segment to the initial target vessel segment.

In one of the embodiments, editing the initial target vessel segment center line based on the edit instruction to obtain the final target vessel segment center line, includes: obtaining an initial target vessel segment center line and initial target vessel segment data of the initial target vessel segment according to the vessel segment identification of the initial target vessel segment; generating combined vessel segment data based on the to-be-added vessel segment data and the initial target vessel segment data; determining a corresponding combined vessel segment center line according to the combined vessel segment data; and generating a final target vessel segment center line based on the initial target vessel segment center line and the combined vessel segment center line.

Specifically, the edit instruction may be the adding instruction, i.e., during the edit for the vessel segment of the detected object, one or more vessel segments are added to the target vessel segment.

In this embodiment, the adding instruction may include the to-be-added vessel segment data of the vessel segment to be added, and the vessel segment identification of the initial target vessel segment, namely Segment ID.

In the present embodiment, the initial target vessel segment center line and the initial target vessel segment data of the initial target vessel segment are acquired according to the vessel segment identification of the initial target vessel segment. The combined vessel segment data are generated based on the to-be-added vessel segment data and the initial target vessel segment data. The corresponding combined vessel segment center line is determined according to the combined vessel segment data. The final target vessel segment center line is generated based on the initial target vessel segment center line and the combined vessel segment center line.

Specifically, according to the vessel segment identification of the initial target vessel segment, the server may choose, from the vessel segment center line set, the initial target vessel segment center line of the initial target vessel segment, which is corresponding to the vessel segment identification of the initial target vessel segment, and may store the initial target vessel segment center line into an intermediate vessel segment center line set, and acquire the initial target vessel segment data from the vessel segment data set, and store the initial target vessel segment data into an intermediate vessel segment data set.

In this embodiment, the server may perform a thinning and skeletonization processing according to the combined vessel segment data, to obtain the combined vessel segment center line.

Further, the server may generate the final target vessel segment center line according to the initial target vessel segment center line and the combined vessel segment center line.

Further, the server may obtain the vessel segment point data from the combined vessel segment data, according to the final target vessel segment center line, and add the vessel segment point data to the intermediate vessel segment data set, to obtain the final target vessel segment data.

In one of the embodiments, the combination vessel segment center line includes a plurality of vessel segment center lines. Generating the final target vessel segment center line according to the initial target vessel segment center line and the combined vessel segment center line includes: obtaining an overlapping relationship according to each combined vessel segment center line and the initial target vessel segment center line; processing the combined vessel segment center lines and the initial target vessel segment center line according to each overlapping relationship; and generating the final target vessel segment center line based on the processed combined center lines and the processed initial target vessel segment center line.

Constructing the corresponding final target vessel segment according to the final target vessel segment center line includes: dividing the combined vessel segment data according to each final target vessel segment center line, and generating vessel segment data of each vessel segment corresponding to each final target vessel segment center line; processing the vessel segment data of each vessel segment according to each overlapping relationship, and obtaining the final target vessel segment data based on the processed vessel segment data and the initial target vessel segment data; constructing the corresponding final target vessel segment based on the final target vessel segment data and the final target vessel segment center line.

In one of the embodiments, processing the combined vessel segment center lines and the initial target vessel segment center line according to each overlapping relationship, and generating the final target vessel segment center line based on the processed combined center lines and the processed initial target vessel segment center line, include: deleting a corresponding vessel segment center line from the combination vessel center line when the overlapping relationship is a full overlap; retaining the vessel segment center line in the combination vessel center line when the overlapping relationship is a non-overlap; retaining the vessel segment center line in the combination vessel center line when the overlapping relationship is a partial overlap, and deleting a center-line point of the overlapped portion from the corresponding initial target vessel segment center line; traversing all vessel segment center lines to obtain an intermediate combined center line and an intermediate target vessel segment center line; and adding the intermediate combined center line to the intermediate initial target vessel segment center line, to obtain the final target vessel segment center line.

Processing the vessel segment data of each vessel segment according to each overlapping relationship, and obtaining the final target vessel segment data based on the processed vessel segment data and the initial target vessel segment data, includes: deleting the initial target vessel segment data corresponding to a full overlap from the combined vessel segment data when the overlap relationship is the full overlap; retaining the vessel segment data corresponding to a non-overlap in the combined vessel segment data when the overlapping relationship is the non-overlap; retaining the vessel segment data in the combination vessel segment when the overlapping relationship is a partial overlap, and deleting the overlapped vessel segment data in the initial target vessel segment data, to obtain an intermediate target vessel segment data, in which the overlapped vessel segment data are deleted; traversing all vessel segment data to obtain updated intermediate combined vessel segment data and updated intermediate target vessel segment data; adding the updated intermediate combined vessel segment data to the updated intermediate target vessel segment data, to obtain the final target vessel segment data.

In one of the embodiments, acquiring the vessel information of the detected object may include: acquiring scanned data of the detected object; dividing the scanned data to acquire original vessel information corresponding to the detected object; performing the thinning and skeletonization processing on the vessel information, to obtain a vessel segment center line corresponding to each vessel segment; and determining, based on each vessel segment center line, vessel segment data corresponding to each vessel segment among original vessel information.

Figure 3:
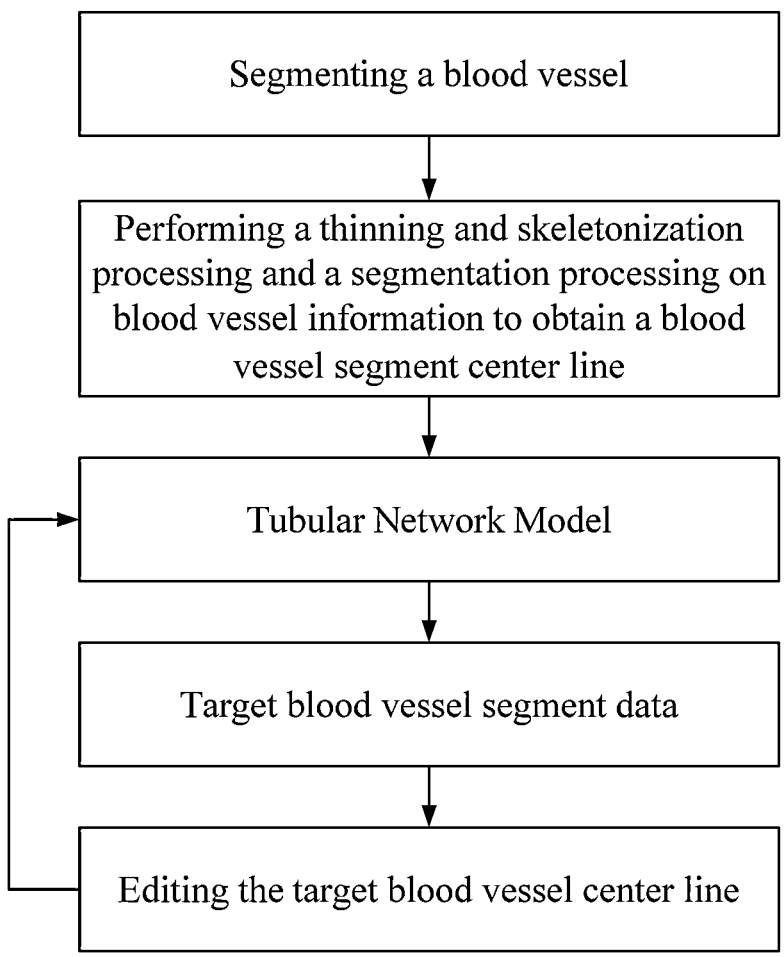
FIG. 3 is a schematic flowchart of the vessel displaying method according to another embodiment of the present disclosure.

Specifically, referring to FIG. 3, the server may scan the detected object by CT, a magnetic resonance detection system, or the like, to acquire the scanned data of the detected object.

Further, the server may segment the scanned data, that is, segment the vessel. For example, the scanned data is segmented by a segmentation method based on deep learning, to obtain the vessel information corresponding to the detected object. The vessel information may include the vessel segment center line of each vessel segment and the vessel segment data of each vessel segment.

In this embodiment, the server may perform the thinning and skeletonization processing and segmentation processing on the original vessel information by using a thinning and skeletonization processing algorithm, to extract the vessel segment center line of each vessel segment.

Further, based on the tubular network model, the server may acquire corresponding target vessel segment data according to the target vessel segment center line, and edit the target vessel center line according to the target vessel segment data.

By traversing all target vessel segment center lines, corresponding target vessel segment data each are acquired based on the tubular network model, and each target vessel center line is edited according to the target vessel segment data.

It should be understood that although the steps in the flowcharts of FIGS. 2 and 3 are shown sequentially as indicated by arrows, these steps are not necessarily performed sequentially as indicated by arrows. Unless expressly stated herein, these steps are not performed in a strict order, and may be performed in other orders. Moreover, at least a portion of the steps in FIGS. 2 and 3 may include a plurality of sub-steps or a plurality of stages, which are not necessarily performed at the same time, but may be performed at different time, and the sub-steps or stages may not necessarily be performed sequentially, but may be performed sequentially or alternately with other steps, or with at least a portion of the sub-steps or stages of other steps.

Figure 4:
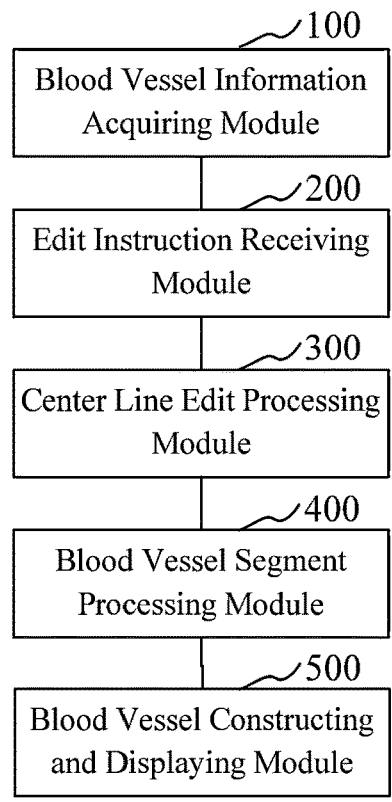
FIG. 4 is a structural block view showing a vessel display device according to an embodiment of the present disclosure.

In an embodiment, as shown in FIG. 4, a vessel display device is provided. The vessel display device includes a vessel information acquiring module 100, an edit instruction receiving module 200, a center line edit processing module 300, a vessel segment processing module 400, and a vessel constructing and displaying module 500.

The vessel information acquiring module 100 is configured to acquire vessel information of a detected object, and the vessel information includes a vessel segment center line and vessel segment data of each vessel segment.

The edit instruction receiving module 200 is configured to receive an edit instruction.

The center line edit processing module 300 is configured to edit an initial target vessel segment center line based on the edit instruction, to obtain a final target vessel segment center line.

The vessel segment processing module 400 is configured to construct a final target vessel segment according to the final target vessel segment center line.

The vessel constructing and displaying module 500 is configured to construct a target vessel based on the final target vessel segment, and display target vessel.

In one of the embodiments, the above edit instruction receiving module 200 is configured to receive a trim instruction, which includes to-be-trimmed region data.

The center line edit processing module 300 includes a first center line acquiring unit, a determining unit, and a first edit unit.

The first center line acquiring unit determines the initial target vessel segment based on the trim instruction, and obtains the initial target vessel segment center line of the initial target vessel segment.

The determining unit is configured to determine whether each initial center-line point of the initial target vessel segment center line is in the to-be-trimmed region data.

The first edit unit is configured to determine that the initial center-line point is a target center-line point corresponding to the trim instruction when the initial center-line point is in the to-be-trimmed region data, and to delete the target center-line point from the initial target vessel segment center line to obtain the final target vessel segment center line.

In one of the embodiments, the vessel segment processing module 400 includes a first vessel segment data acquiring unit, a first deleting unit, and a first constructing unit.

The first vessel segment data acquiring unit is configured to obtain the initial target vessel segment data corresponding to the initial target vessel segment.

The first deleting unit is configured to delete initial vessel segment point data corresponding to the to-be-trimmed region data from the initial target vessel segment data, to obtain the final target vessel segment data.

The first constructing unit is configured to construct a corresponding final target vessel segment according to the final target vessel segment data and the final target vessel segment center line.

In one of the embodiments, the edit instruction receiving module 200 above is configured to receive a modification instruction. The modification instruction includes the vessel segment identification of the initial target vessel segment to be modified and the to-be-modified region data.

The center line edit processing module 300 includes a second center line acquiring unit, a dividing unit, and a first modifying unit.

The second center line acquiring unit is configured to obtain an initial target vessel segment center line of an initial target vessel segment to be modified according to the vessel segment identification.

The dividing unit is configured to divide the initial target vessel segment center line according to the to-be-modified region data, to obtain the initial first center line corresponding to the to-be-modified region data and a second center line without modification.

The first modifying unit is configured to perform a processing of modifying the vessel name and/or the vessel segment identification of the initial first center line, to obtain a final first center line.

In one of the embodiments, the vessel segment processing module 400 above includes a second vessel segment data acquiring unit, an extracting unit, a second deleting unit, a second modifying unit, and a second constructing unit.

The second vessel segment data acquiring unit is configured to obtain initial target vessel segment data of an initial target vessel segment to be modified according to the vessel segment identification.

The extracting unit is configured to extract vessel segment point data corresponding to the to-be-modified region data from the initial target vessel segment data, to obtain initial first vessel segment data to be modified.

The second deleting unit is configured to delete the initial first vessel segment data from the initial target vessel segment data, to obtain second vessel segment data without modification.

The second modifying unit is configured to modify the vessel name and/or the vessel segment identification in the initial first vessel segment data, to obtain final first vessel segment data.

The second constructing unit is configured to construct a final first target vessel segment according to the final first center line and the final first vessel segment data, and construct a second target vessel segment according to the second center line and the second vessel segment data.

In one of the embodiments, the edit instruction receiving module 200 is configured to receive an adding instruction. The adding instruction includes to-be-added vessel segment data of a to-be-added vessel segment, and the vessel segment identification of the initial target vessel segment.

The center line edit processing module 300 includes a third center line acquiring unit, a generating unit, a third vessel segment data acquiring unit, and a third constructing unit.

Third center line acquiring unit is configured to obtain an initial target vessel segment center line and initial target vessel segment data of the initial target vessel segment according to the vessel segment identification of the initial target vessel segment.

The generating unit is configured to generate combined vessel segment data based on the to-be-added vessel segment data and the initial target vessel segment data.

The third vessel segment data acquiring unit is configured to determine a corresponding combined vessel segment center line according to the combined vessel segment data.

The third constructing unit is configured to generate a final target vessel segment center line based on the initial target vessel segment center line and the combined vessel segment center line.

In one of the embodiments, the vessel information acquiring module 100 includes a scanned data acquiring unit, a segmentation unit, a skeletonizing unit, and a vessel segment data acquiring unit.

The scanned data acquiring unit is configured to acquire scanned data of the detected object.

The segmentation unit is configured to divide the scanned data to acquire the vessel information corresponding to the detected object.

The skeletonizing unit is configured to perform the thinning and skeletonization processing on the vessel information, to obtain a vessel segment center line corresponding to each vessel segment.

The vessel segment data acquiring unit is configured to, based on each vessel segment center line, determine vessel segment data among the original vessel information corresponding to each vessel segment.

In one of the embodiments, the display module 500 is further configured to acquire vessel segment center lines and corresponding vessel segment data of all non-target vessel segments, and construct all non-target vessel segments based on the vessel segment center lines and the corresponding vessel segment data of the non-target vessel segments.

For specific limitations of the vessel display device, reference may be made to the limitations of the vessel displaying method above, and the specific limitations will not be described repeatedly hereinafter. The various modules in the vessel display device may be implemented in whole or in part by software, hardware, and combinations thereof. The various modules may be embedded in or independent of a processor of a computer device by means of hardware, or may be stored in a memory of the computer device by means of software, so that the processor calls and executes the operations corresponding to the various modules above.

Figure 5:
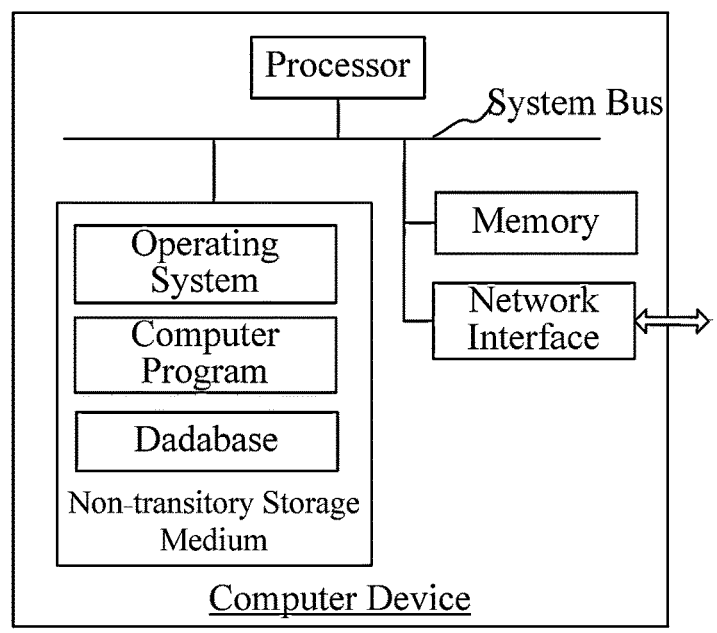
FIG. 5 is a view showing an internal structure of a computer device according to an embodiment of the present disclosure.

In one of the embodiments, a computer device is provided. The computer device may be a server, the internal structure of which is shown in FIG. 5. The computer device includes a processor, a memory, a network interface, and a database which are connected by a system bus. The processor of the computer device is configured to provide computing and control capabilities. The memory of the computer device includes a non-transitory storage medium and a memory. The non-transitory storage medium stores an operating system, a computer program, and a database. The memory provides an environment for the operation of an operating system and a computer program in a non-transitory storage medium. The database of the computer device is configured to store data such as the vessel information and the edit instruction. The network interface of the computer device is configured to communicate with external terminals through a network connection. The computer program, when executed by a processor, implements the vessel displaying method.

It should be understood by those skilled in the art that the structure shown in FIG. 5 is a block diagram showing only part of the structure associated with the solutions of the present application, but not intend to limit the computer device to which the solutions of the present application are applied, and that the particular computer device may include more or less components than those shown in the drawings, or may combine with certain components, or may have different component arrangements.

In one of the embodiments, a computer device is provided. The computer device includes a memory and a processor. A computer program is stored in the memory, and when executing the computer program, the processor performs steps of: acquiring vessel information of a detected object, and the vessel information including a vessel segment center line and vessel segment data of each vessel segment; receiving an edit instruction; editing an initial target vessel segment center line based on the edit instruction, to obtain a final target vessel segment center line; constructing a final target vessel segment according to the final target vessel segment center line; constructing a target vessel based on the final target vessel segment, and displaying the target vessel.

In one of the embodiments, the receiving the edit instruction, which is performed by the processor when executing the computer program, includes receiving a trim instruction. The trim instruction includes to-be-trimmed region data. The editing the initial target vessel segment center line based on the edit instruction to obtain the final target vessel segment center line, which is performed by the processor when executing the computer program, includes: determining the initial target vessel segment based on the trim instruction, and obtaining the initial target vessel segment center line of the initial target vessel segment; determining whether each initial center-line point of the initial target vessel segment center line is in the to-be-trimmed region data; and it is determined that the initial center-line point is a target center-line point corresponding to the trim instruction when the initial center-line point is in the to-be-trimmed region data, and deleting the target center-line point from the initial target vessel segment center line to obtain the final target vessel segment center line.

In one of the embodiments, the constructing the final target vessel segment according to final target vessel segment center line, which is performed by the processor when executing the computer program, includes: obtaining the initial target vessel segment data corresponding to the initial target vessel segment; deleting initial vessel segment point data corresponding to the to-be-trimmed region data from the initial target vessel segment data to obtain the final target vessel segment data; and constructing a corresponding final target vessel segment according to the final target vessel segment data and the final target vessel segment center line.

In one of the embodiments, the receiving the edit instruction, which is performed by the processor when executing the computer program, includes receiving a modification instruction. The modification instruction includes the vessel segment identification of the initial target vessel segment to be modified and the to-be-modified region data. The editing an initial target vessel segment center line based on the edit instruction to obtain a final target vessel segment center line, which is performed by the processor when executing the computer program, includes: obtaining an initial target vessel segment center line of an initial target vessel segment to be modified according to the vessel segment identification; dividing the initial target vessel segment center line according to the to-be-modified region data, to obtain the initial first center line corresponding to the to-be-modified region data and a second center line without modification; and performing a processing of modifying the vessel name and/or the vessel segment identification of the initial first center line, to obtain a final first center line.

In one of the embodiments, the constructing the final target vessel segment according to the final target vessel segment center line, which is performed by the processor when executing the computer program, includes: obtaining initial target vessel segment data of an initial target vessel segment to be modified according to the vessel segment identification; extracting vessel segment point data corresponding to the to-be-modified region data, from the initial target vessel segment data, to obtain initial first vessel segment data to be modified; deleting the initial first vessel segment data from the initial target vessel segment data, to obtain second vessel segment data without modification; modifying the vessel name and/or the vessel segment identification in the initial first vessel segment data, to obtain final first vessel segment data; and constructing a final first target vessel segment according to the final first center line and the final first vessel segment data, and constructing a second target vessel segment according to the second center line and the second vessel segment data.

In one of the embodiments, the receiving the edit instruction, which is performed by the processor when executing the computer program, includes receiving an adding instruction. The adding instruction may include the to-be-added vessel segment data of the vessel segment to be added, and the vessel segment identification of the initial target vessel segment. The editing the initial target vessel segment center line based on the edit instruction to obtain the final target vessel segment center line, includes: obtaining an initial target vessel segment center line and initial target vessel segment data of the initial target vessel segment according to the vessel segment identification of the initial target vessel segment; generating combined vessel segment data based on the to-be-added vessel segment data and the initial target vessel segment data; determining a corresponding combined vessel segment center line according to the combined vessel segment data; and generating a final target vessel segment center line based on the initial target vessel segment center line and the combined vessel segment center line.

In one of the embodiments, the acquiring the vessel information of the detected object, which is performed by the processor when executing the computer program, includes: acquiring scanned data of the detected object; dividing the scanned data to obtain original vessel information corresponding to the detected object; performing the thinning and skeletonization processing on the vessel information, to obtain a vessel segment center line corresponding to each vessel segment; and based on each vessel segment center line, determining vessel segment data among the original vessel information corresponding to each vessel segment.

In one of the embodiments, the processor, when executing the computer program, further performs steps of: acquiring vessel segment center lines and corresponding vessel segment data of all non-target vessel segments; and constructing all non-target vessel segments based on the vessel segment center lines and the corresponding vessel segment data of the non-target vessel segments.

In one of the embodiments, a computer readable storage medium is provided. The computer readable storage medium has a computer program stored thereon, and the computer program, when executed by a processor, performs steps of: acquiring vessel information of a detected object, and the vessel information including a vessel segment center line and vessel segment data of each vessel segment; receiving an edit instruction; editing an initial target vessel segment center line based on the edit instruction, to obtain a final target vessel segment center line; constructing a final target vessel segment according to the final target vessel segment center line; constructing a target vessel based on the final target vessel segment, and displaying the target vessel.

In one of the embodiments, the receiving the edit instruction, which is performed by the computer program when executed by the processor, includes receiving a trim instruction. The trim instruction includes to-be-trimmed region data. The editing the initial target vessel segment center line based on the edit instruction to obtain the final target vessel segment center line, which is performed by the computer program when executed by the processor, includes: determining the initial target vessel segment based on the trim instruction, and obtaining the initial target vessel segment center line of the initial target vessel segment; determining whether each initial center-line point of the initial target vessel segment center line is in the to-be-trimmed region data; and it is determined that the initial center-line point is a target center-line point corresponding to the trim instruction when the initial center-line point is in the to-be-trimmed region data, and deleting the target center-line point from the initial target vessel segment center line to obtain the final target vessel segment center line.

In one of the embodiments, the constructing the final target vessel segment according to final target vessel segment center line, which is performed by the computer program when executed by the processor, includes: obtaining the initial target vessel segment data corresponding to the initial target vessel segment; deleting initial vessel segment point data corresponding to the to-be-trimmed region data from the initial target vessel segment data to obtain the final target vessel segment data; constructing a corresponding final target vessel segment according to the final target vessel segment data and the final target vessel segment center line.

In one of the embodiments, the receiving the edit instruction, which is performed by the computer program when executed by the processor, includes receiving a modification instruction. The modification instruction includes the vessel segment identification of the initial target vessel segment to be modified and the to-be-modified region data. The editing an initial target vessel segment center line based on the edit instruction to obtain a final target vessel segment center line, which is performed by the processor when executing the computer program, includes: obtaining an initial target vessel segment center line of an initial target vessel segment to be modified according to the vessel segment identification; dividing the initial target vessel segment center line according to the to-be-modified region data, to obtain the initial first center line corresponding to the to-be-modified region data and a second center line without modification; and performing a processing of modifying the vessel name and/or the vessel segment identification of the initial first center line, to obtain a final first center line.

In one of the embodiments, the constructing the final target vessel segment according to final target vessel segment center line, which is performed by the computer program when executed by the processor, includes: obtaining initial target vessel segment data of an initial target vessel segment to be modified according to the vessel segment identification; extracting vessel segment point data corresponding to the to-be-modified region data from the initial target vessel segment data, to obtain initial first vessel segment data to be modified; deleting the initial first vessel segment data from the initial target vessel segment data, to obtain second vessel segment data without modification; modifying the vessel name and/or the vessel segment identification in the initial first vessel segment data, to obtain final first vessel segment data; and constructing a final first target vessel segment according to the final first center line and the final first vessel segment data, and constructing a second target vessel segment according to the second center line and the second vessel segment data.

In one of the embodiments, the receiving the edit instruction, which is performed by the computer program when executed by the processor, includes receiving an adding instruction. The adding instruction may include the to-be-added vessel segment data of the vessel segment to be added, and the vessel segment identification of the initial target vessel segment. The editing the initial target vessel segment center line based on the edit instruction to obtain the final target vessel segment center line, includes: obtaining an initial target vessel segment center line and initial target vessel segment data of the initial target vessel segment according to the vessel segment identification of the initial target vessel segment; generating combined vessel segment data based on the to-be-added vessel segment data and the initial target vessel segment data; determining a corresponding combined vessel segment center line according to the combined vessel segment data; and generating a final target vessel segment center line based on the initial target vessel segment center line and the combined vessel segment center line.

In one of the embodiments, the acquiring the vessel information of the detected object, which is performed by the computer program when executed the processor, includes: acquiring scanned data of the detected object; dividing the scanned data to acquire original vessel information corresponding to the detected object; performing the thinning and skeletonization processing on the vessel information, to obtain a vessel segment center line corresponding to each vessel segment; and based on each vessel segment center line, determining vessel segment data among the original vessel information corresponding to each vessel segment.

In one of the embodiments, the computer program, when executed by the processor, further performs steps of: acquiring vessel segment center lines and corresponding vessel segment data of all non-target vessel segments; and constructing all non-target vessel segments based on the vessel segment center lines and the corresponding vessel segment data of the non-target vessel segments.

In one of the embodiments, a computer program product is provided. The computer program product includes a computer program. The computer program, when executed by a processor, performs the steps in each of the method embodiments described above.

Lumen structures of vessels in the human body are often subject to various problems such as plaque and angiostenosis, and it is often medically necessary to evaluate a state of a vessel. The vessel center line is an important basis for the applications of a curved surface development of the vessel, a cross-section inspection for the vessel, and a guidance for a clinical surgical. Since the structure of the human body is relatively complex, there may be an error in the vessel center line extracted from medical images, and the vessel center line needs to be corrected.

In some embodiments of the present application, in order to further improve the accuracy of the target vessel center line, after the final target vessel is constructed and displayed, a position of the target vessel center line may be further adjusted to correct the error. The terminal may display a medical image of a corresponding portion, which makes it easy to select the corresponding vessel center line and adjust the position of the vessel center line.

In some embodiments, the terminal acquires scanned medical data and construct an image based on the medical data to obtain a three-dimensional image. In the three-dimensional image, various portions in the three-dimensional image are displayed by means of a stereoscopic structure, so that a vessel center-line point set is viewed in the stereoscopic structure based on the viewing-ray direction, thereby adjusting the vessel center line.

Figure 6:
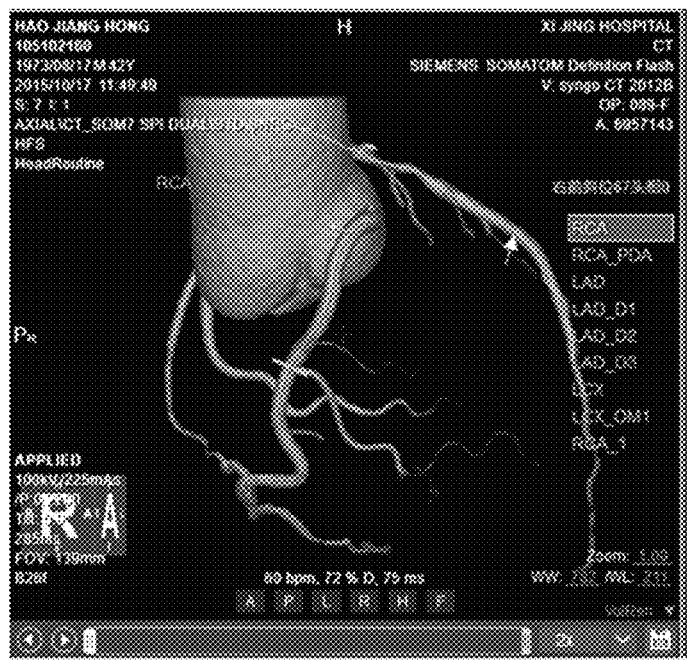
FIG. 6 is a schematic diagram of an interface for adjusting a position of a target vessel center line according to an embodiment of the present disclosure.

FIG. 6 is a schematic diagram of an interface for adjusting a position of a target vessel center line according to an embodiment of the present disclosure. As shown in FIG. 6, the three-dimensional image includes graphic elements of all center lines, but only the selected vessel center line is displayed. When the mouse moves to a position of the three-dimensional image and the terminal detects a presence of a vessel center line, the vessel center line is automatically presented, then the terminal may receive a position adjustment instruction for the vessel center line. When the user selects one center line, the optimal viewing angle for viewing the current center line is automatically calculated, and the current center line is displayed at the optimal viewing angle.

Figure 7:
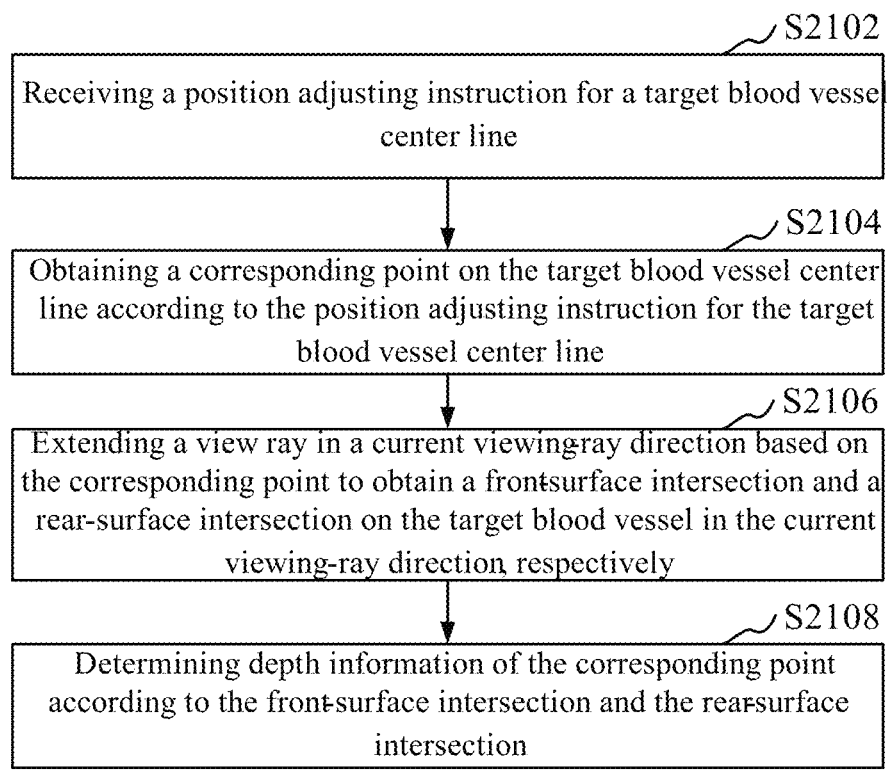
FIG. 7 is a schematic flowchart of a method for adjusting a position of a target vessel center line according to an embodiment of the present disclosure.

In some embodiments, after the constructing the target vessel based on the final target vessel segment and displaying the target vessel, the vessel displaying method of the present application further includes the following steps S2102 to S2108, as shown in FIG. 7. The embodiments of the method are illustrated by taking the method applied to the terminal for an example. It should be understood that the method may also be applied to the server, or may also be applied to a system including the terminal and the server, and may be implemented through an interaction between the terminal and the server.

In step S2102, a position adjusting instruction for the target vessel center line is received.

In step S2104, a corresponding point on the target vessel center line is obtained according to the position adjusting instruction for the target vessel center line.

Specifically, the vessel center line is composed of numerous points, and when it is determined that there is an error in the vessel center line, the position of the vessel center line may be adjusted. For example, a point on the target vessel center line, at which an error exists, is selected as a corresponding point to adjust the position of the target vessel center line and modify a trajectory of the vessel center line, that is, adjusting the position of the target vessel center line, which includes re-determining a position of the target vessel center-line point. The position of the target vessel center line may include a position located in the center of the vessel in the viewing field, but also located in the center of the vessel in a depth direction of the vessel. For the vessel center-line point being located in the center of the vessel in the viewing field, it may be directly judged by the user.

In step S2106, a view ray is extended in a current viewing-ray direction based on the corresponding point to obtain a front-surface intersection and a rear-surface intersection on the target vessel in the current viewing-ray direction, respectively.

Figure 8:
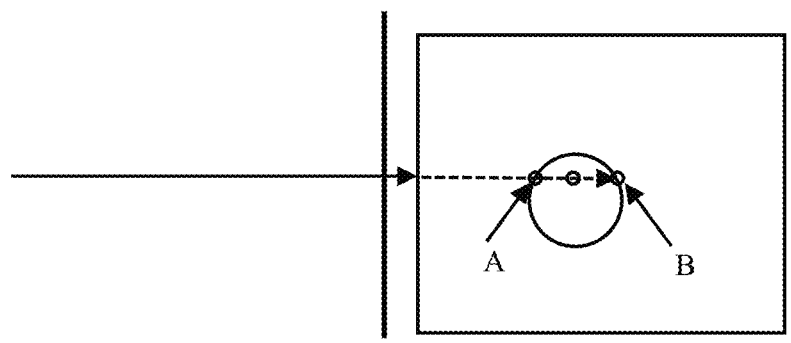
FIG. 8 is a schematic view showing a front-surface intersection and a rear-surface intersection of a target vessel according to an embodiment of the present disclosure.

Specifically, the current viewing-ray direction refers to a direction perpendicular to the screen and pointing to the image. An intersection of the viewing ray and the image is the target vessel center-line point on the current screen. As shown in FIG. 8, the viewing ray emits to the three-dimensional image in the current viewing-ray direction. In the current viewing-ray direction, the front-surface intersection A, at which the viewing ray intersects with the front surface of the target vessel, and the rear-surface intersection B, at which the viewing ray intersects with the rear surface of the target vessel, are detected.

In step S2108, depth information of the corresponding point is determined according to the front-surface intersection and the rear-surface intersection.

Specifically, the front-surface intersection on the target vessel in the current viewing-ray direction is the first intersection where the viewing ray intersects with the target vessel in the viewing-ray direction. Similarly, the rear-surface intersection on the target vessel in the current viewing-ray direction is the last intersection where the viewing ray intersects with the target vessel in the viewing-ray direction.

The depth information is calculated according to a distance between the front-surface intersection and the rear-surface intersection, so that a thickness of the target vessel may be calculated according to the distance between the front-surface intersection and the rear-surface intersection, and the depth information of the center-line point on the center line may be calculated based on the thickness of the target vessel. For example, the depth is a half of the distance between the front-surface intersection and the rear-surface intersection. Thus, a position-adjusted target vessel center line point O may be obtained. That is, a position of a center point of a line connecting the front-surface intersection and the rear-surface intersection of target vessel is calculated as a position of the position-adjusted target vessel center line point.

In an embodiment of the present application, after the position adjusting instruction for the target vessel center line is received, the corresponding point is first determined, and the trajectory information is adjusted, and then the front-surface intersection and the rear-surface intersection of the target vessel in the current viewing-ray direction are obtained based on the current viewing-ray direction, so that the depth information may be obtained based on the front-surface intersection and the rear-surface intersection, thereby automatically determining the depth of the center-line point at the adjusted position, ensuring that the point is in the center of the vessel, correcting the center line quickly, accurately and completely, and improving the convenience of the position adjustment for the center line.

In some of the embodiments, the adjusting the position of the target vessel center line may be an independent scheme. That is, in some embodiments, the present disclosure provides a method for adjusting a position of a target vessel center line, which is independent of any one of the vessel displaying methods described herein. The method for adjusting the position of the target vessel center line includes the steps S2102 to S2108 above.

In one of the embodiments, extending the viewing ray based on the corresponding point in the current viewing-ray direction includes: acquiring the current viewing-ray direction, and the front-surface intersection and the rear-surface intersection on the target vessel in the current viewing-ray direction; generating a unit vector according to the front-surface intersection and the rear-surface intersection; and extending the viewing ray along the unit vector direction sequentially by at least one unit vector length from the corresponding point.

Figure 9:
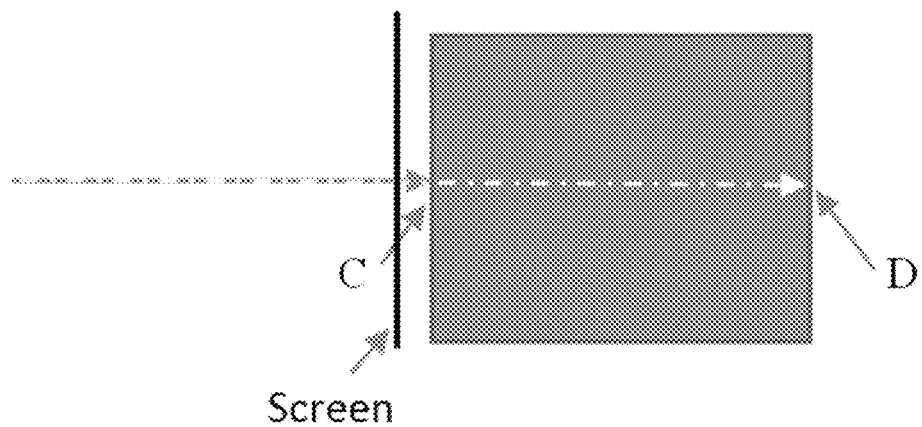
FIG. 9 is a schematic view showing a front-surface intersection and a rear-surface intersection of a target vessel according to another embodiment of the present disclosure.

Specifically, the current viewing-ray direction is the direction pointing the image and perpendicular to the screen. The front-surface intersection and the rear-surface intersection on the target vessel in the current viewing-ray direction are shown as the front-surface intersection C and the rear-surface intersection D in FIG. 9.

A viewing ray vector is calculated according to the front-surface intersection and the rear-surface intersection on the target vessel in the current viewing-ray direction as follows:

$$vRayLine = ptRayEnd - ptRayStart$$

where, ptRayStart denotes the front-surface intersection of the viewing ray and the front surface of the target vessel, and ptRayEnd denotes the rear-surface intersection of the viewing ray and the rear surface of the target vessel. A vector norm $|vRayLine|$, and the unit vRayLine vector $x = vRayLine/|vRayLine|$ are calculated.

Starting from the front-surface intersection, the viewing ray is extended along the viewing ray vector direction by one unit vector length after another, till the viewing ray penetrates the target vessel to realize the extension based on the corresponding point.

In one of the embodiments, the vessel displaying method of the present application further includes: acquiring a previous center-line point of the corresponding point on the target vessel center line, when the viewing ray extended along the current viewing-ray direction based on the corresponding point does not contact the vessel tissue; and using depth information of the previous center-line point as the depth information of the corresponding point.

When the viewing ray extended along the current viewing-ray direction based on the corresponding point first contacts the vessel, as shown in FIG. 6 (whether tissues not shown in the current three-dimensional image are contacted or not is not considered), the viewing ray is extended along the viewing-ray direction continually till it reaches the rear surface of the vessel. The position of the center point of the line connecting the front-surface intersection and the rear-surface intersection on the target vessel is calculated as the position of the position-adjusted center-line point.

When the viewing ray extended along the current viewing-ray direction based on the corresponding point does not contact the vessel tissue, the depth information of the previous center-line point on the target vessel is used as the depth of the corresponding point.

Figure 10:
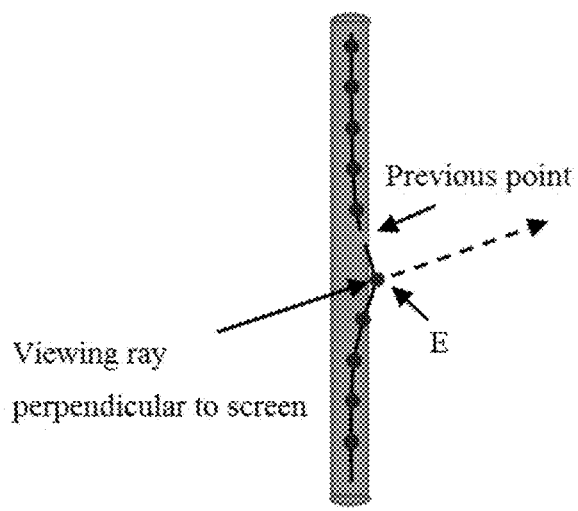
FIG. 10 is a schematic view showing one center-line point located outside the target vessel according to an embodiment of the present disclosure.

For example, since the coronary artery vessel is thin, when the center line is manually adjusted, the position of the center-line point is easily to be adjusted to the outside of the coronary artery, and it is necessary to ensure that a depth deviation of the center-line point outside the coronary artery is controllable, so that the point is subsequently adjusted back to a correct position. Specifically, as shown in FIG. 10, in this embodiment, an adjustment error causes the center line position to be adjusted to the outside of the vessel, and the viewing ray emits from a point E, but the viewing ray does not penetrate the vessel, then the depth information of the previous center-line point on the vessel center line is used as the depth information of the point E.

In one of the embodiments, the vessel displaying method of the present application further includes: acquiring a preset length when the viewing ray extended along the current viewing-ray direction based on the corresponding point contacts a non-vessel tissue first; acquiring a target point at which the current viewing ray intersects with the non-vessel tissue, and determining whether a length extended based on the target point along the current viewing-ray direction is less than the preset length; when the length extended based on the target point in the current viewing-ray direction is less than the preset length, continuing to extend the viewing ray in the current viewing-ray direction based on the target point, till the viewing ray contacts the vessel tissue to obtain the front-surface intersection and the rear-surface intersection on the target vessel; and calculating the depth information of the corresponding point according to the front-surface intersection and the rear-surface intersection.

In one of the embodiments, the vessel displaying method of the present application further includes: acquiring the previous center-line point of the corresponding point on the vessel center line, when the length extended based on the target point in the current viewing-ray direction is greater than or equal to the preset length; using the depth information of the previous center-line point as the depth information of the corresponding point.

Figure 11:
FIG. 11 is a schematic view showing part of a target vessel embedded in a superficial layer of a heart according to an embodiment of the present disclosure.
Figure 12:
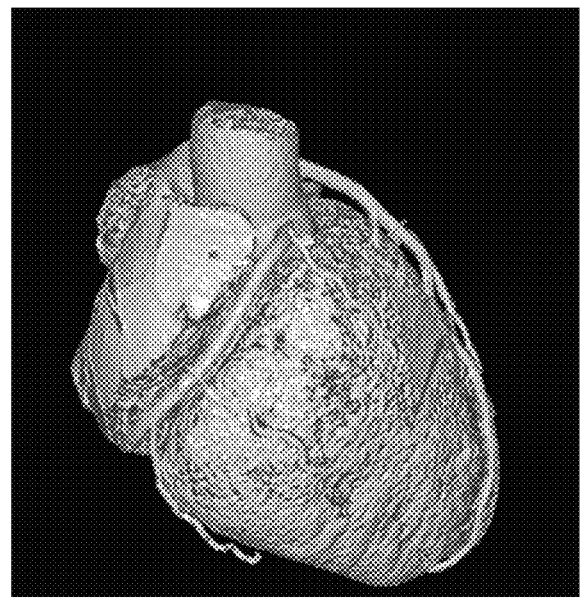
FIG. 12 is a schematic view showing part of a target vessel blocked by other tissues according to an embodiment of the present disclosure.

If other visible tissues other than the vessel are first contacted, a tolerance of a preset length of N units is allowed and a tracking may continue in a depth direction, which aims at preventing some special situations such as: the coronary arteries on the heart surface may not all appear on the surfaces of the heart ventricle, atrium cordis, and cardiac muscle, and part of the vessels may be embedded in the superficial layer of the heart; or in the current viewing angle, the vessel is blocked by other tissues. As shown in FIG. 11, part of vessels may be embedded in the superficial layer of the heart. As shown in FIG. 12, in the current viewing angle, the vessel is blocked by other tissues.

The value N is obtained by a thickness Thickness (mm) of a blocking tissue being divided by a voxel space Spacing (an actual physical length represented by one voxel in the medical image voxel data), i.e. N=Thickiness/Spacing, which is acceptable empirically.

Figure 13:
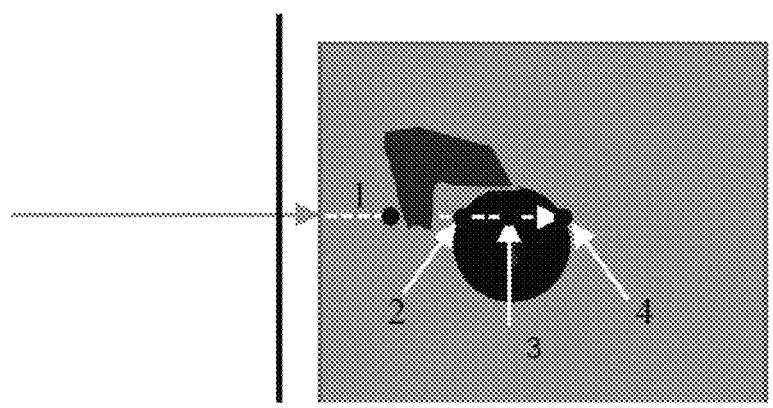
FIG. 13 is a schematic view showing the front-surface intersection and the rear-surface intersection of the target vessel according to another embodiment of the present disclosure.

Specifically, as shown in FIG. 13, the viewing ray extended along the current viewing-ray direction based on the corresponding point (a point 3 in the figure) contacts the non-vessel tissue first, an intersection at which the current viewing ray intersects with the non-vessel tissue, i.e., the target point, namely a point 1 in the FIG. 13, is obtained. Then the current viewing ray is extended continually, and it is determined whether the length extended along the current viewing-ray direction based on the target point is less than the preset length. If the length extended from the point 1 is less than the preset length, the viewing ray is extended continually until it contacts the front surface of the vessel (at a point 2). It is determined whether the length from the point 1 to the point 2, i.e., the distance between the target point, namely the point 1, and the front-surface intersection, namely the point 2, on the target vessel, which are in the current viewing-ray direction, is less than the preset length. If the length from the point 1 to the point 2 is less than the preset length, then the depth information is calculated according to the point 1 and the point 2. If the length from the point 1 to the point 2 is greater than or equal to the preset length, the previous center-line point of the corresponding point on the target vessel center line is acquired, and the depth information of the previous center-line point is used as the depth information of the corresponding point.

In one of the embodiments, before the receiving the position adjusting instruction for the target vessel center line, the vessel displaying method of the present application further includes: receiving a selecting instruction for the target vessel center line through the target vessel image; adjusting a viewing angle of the display of the target vessel image according to the target vessel center line selected based on the selecting instruction for the target vessel center line.

Specifically, the selecting instruction for the target vessel center line is received through the target vessel image, and the corresponding center line is selected, then a point on the center line is adjusted. After the center line is selected, in order to facilitate viewing, the terminal adjusts the viewing angle of the display of the target vessel image according to the selected target vessel center line.

In one of the embodiment, the adjusting the viewing angle of the display of the target vessel image according to the target vessel center line selected based on the selecting instruction for the target vessel center line, includes: computing a target position of the target vessel image, a first feature point of the target vessel, and a second feature point of a branch to which the selected target vessel center line belongs; calculating a viewing ray vector based on the first feature point of the target vessel and the second feature point of the branch to which the selected target vessel center line belongs; simulating a rotation of the target vessel image at the target position of the target vessel image, and acquiring a rotation angle when the viewing ray vector is perpendicular to the screen inward; and adjusting the viewing angle of the display of the target vessel image based on the rotation angle.

In an embodiment, the target position of the target vessel image is a central point. In other embodiments, the target position may also be selected to be a quarter point or the like, which is not specifically limited herein. In an embodiment, the first feature point of the target vessel, and the second feature point of the branch to which the selected target vessel center line belongs are also central points. In other embodiments, the first feature point and the second feature point may also be selected to be quarter points or the like, which is not specifically limited herein.

Figure 14:
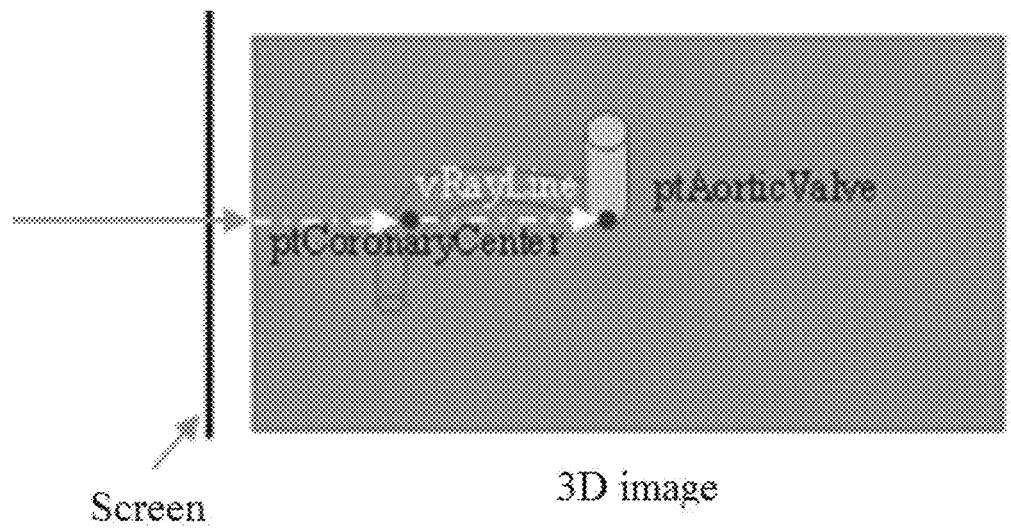
FIG. 14 is a schematic view showing an adjustment of a display viewing angle according to an embodiment of the present disclosure.

Specifically, as shown in FIG. 14, a center point ptCenter of the three-dimensional image and a center point ptAorticValve of the aortic valve are found based on the segmentation result, and then a central point ptCoronaryCenter of the coronary artery branch to which the target center line belongs is found.

The viewing ray vector is calculated according to the center point of the aortic valve and the center point of the coronary branch:

$$VRayLine = ptAorticValve - ptCoronaryCenter$$

The current position of the center point ptCenter of the three-dimensional image and the size of the display of the three-dimensional image are kept unchanged, and the rotation of the image is simulated until the viewing ray vector vRayLine is inwardly perpendicular to the screen, thus obtaining an orientation angle corresponding to the center line. The viewing angle of the three-dimensional image is switched according to the calculated orientation angle.

In one of the embodiments, after the obtaining the corresponding point on the target vessel center line according to the position adjusting instruction for the target vessel center line, the method further includes: adjusting trajectory information of the corresponding point. After determining the depth information of the corresponding point according to the front-surface intersection and the rear-surface intersection, the method further includes adjusting the depth information of the corresponding point.

Specifically, the corresponding point on the target vessel center line is acquired according to the position adjusting instruction for the target vessel center line, the terminal adjusts the trajectory information of the corresponding point according to an input of the user, and the terminal automatically calculates the depth information of the corresponding point whose trajectory information has been adjusted, and adjusts the depth information of the corresponding point according to the calculated depth information, thereby completing a whole position adjustment process.

In the embodiments above, a trend of the center line may be conveniently viewed on the three-dimensional image of VR or Mesh, and the center line may be adjusted and modified directly on the three-dimensional image, thereby greatly improving the convenience and accuracy of adjusting the position of the center line.

It should be understood that, although the steps in the flow charts of the embodiments above are shown sequentially as indicated by the arrows, these steps are not necessarily performed sequentially as indicated by the arrows. Unless expressly stated herein, these steps are not performed in a strict order and may be performed in other orders. Moreover, at least a portion of the steps in the flowcharts of the above embodiments may include a plurality of steps or a plurality of stages, which are not necessarily performed at the same time, but may be performed at different time, and the steps or stages may not necessarily be performed sequentially, but may be performed sequentially or alternately with other steps, or with at least a portion of the steps or stages of other steps.

Based on the same inventive concept, the embodiments of the present application also provide a position adjusting device for the three-dimensional target vessel center line to implement the position adjusting instruction for the three-dimensional target vessel center line above. The solutions to the problems provided by the position adjustment device are similar to the solutions for implementing the position adjustment instruction described above, therefore, for specific limitations in one or more embodiments of the position adjusting device for the three-dimensional target vessel center line provided hereinafter, reference may be made to the above limitations of the position adjustment for the three-dimensional target vessel center line, and they will not be described repeatedly herein.

Figure 15:
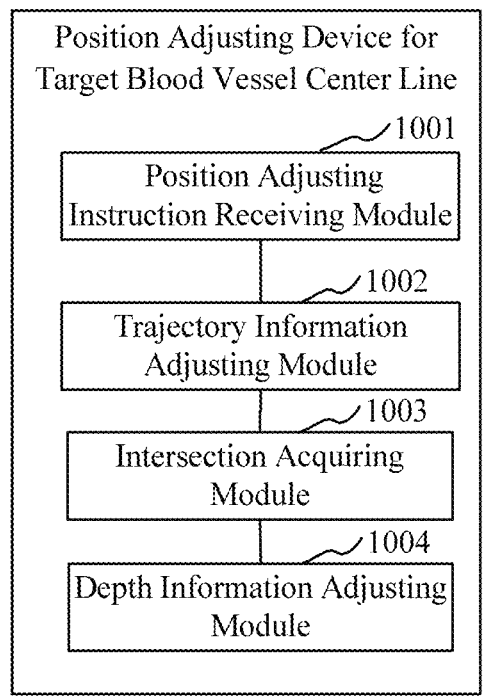
FIG. 15 is a structural block view showing a device for adjusting a position of a target vessel center line of according to an embodiment of the present disclosure.

In one of the embodiments, as shown in FIG. 15, a position adjusting device for a target vessel center line includes a position adjusting instruction receiving module 1001, a trajectory information adjusting module 1002, an intersection acquiring module 1003, and a depth information adjusting module 1004.

The position adjusting instruction receiving module 1001 is configured to receive a position adjusting instruction for the target vessel center line.

The trajectory information adjusting module 1002 is configured to obtain a corresponding point on the target vessel center line according to the position adjusting instruction for the target vessel center line.

The intersection acquiring module 1003 is configured to extend a view ray in a current viewing-ray direction based on the corresponding point to obtain a front-surface intersection and a rear-surface intersection on the target vessel in the current viewing-ray direction, respectively.

The depth information adjusting module 1004 is configured to determine depth information of the corresponding point according to the front-surface intersection and the rear-surface intersection.

In one of the embodiments, the intersection acquiring module 1003 includes an intersection acquiring unit, a vector generating unit, and an extending unit.

The intersection acquiring unit is configured to acquire the current viewing-ray direction, and the front-surface intersection and the rear-surface intersection on the target vessel in the current viewing-ray direction.

The vector generating unit is configured to generate a unit vector according to the front-surface intersection and the rear-surface intersection.

The extending unit is configured to extend the viewing ray along the unit vector direction sequentially by at least one unit vector length from the corresponding point.

In one of the embodiments, the position adjusting device for the three-dimensional target vessel center line further includes a first depth information acquiring module.

The first depth information acquiring module is configured to acquire a previous center-line point of the corresponding point on the target vessel center line when the viewing ray extended along the current viewing-ray direction based on the corresponding point does not contact the vessel tissue, and to use depth information of the previous center-line point as the depth information of the corresponding point.

In one of the embodiments, the position adjusting device for three-dimensional target vessel center line further includes a preset length acquiring module, a determining module, and a second depth information acquiring module.

The preset length acquiring module is configured to acquire a preset length when the viewing ray extended along the current viewing-ray direction based on the corresponding point contacts a non-vessel tissue first.

The determining module is configured to acquire a target point at which the current viewing ray intersects with the non-vessel tissue, and configured to determine whether a length extended based on the target point along the current viewing-ray direction is less than the preset length.

The second depth information acquiring module is configured to continue to extend the viewing ray in the current viewing-ray direction based on the target point when the length extended based on the target point in the current viewing-ray direction is less than the preset length, till the viewing ray contacts the vessel tissue to obtain the front-surface intersection and the rear-surface intersection on the target vessel, and configured to calculate the depth information of the corresponding point according to the front-surface intersection and the rear-surface intersection.

In one of the embodiments, the position adjusting device for the three-dimensional target vessel center line further includes a third depth information acquiring module.

The third depth information acquiring module is configured to acquire the previous center-line point of the corresponding point on the vessel center line when the length extended based on the target point in the current viewing-ray direction is greater than or equal to the preset length, and configured to use the depth information of the previous center-line point as the depth information of the corresponding point.

In one of the embodiments, the position adjusting device for the three-dimensional target vessel center line further includes a selecting instruction receiving module and a viewing angle adjusting module.

The selecting instruction receiving module is configured to receive a selecting instruction for the target vessel center line through the target vessel image.

The viewing angle adjusting module is configured to adjust a viewing angle of the display of the target vessel image according to the target vessel center line selected based on the selecting instruction for the target vessel center line.

In one of the embodiments, the viewing angle adjusting module includes a feature point calculating unit, a viewing ray vector calculating unit, a rotation angle calculating unit, and a viewing angle adjusting unit.

The feature point calculating unit is configured to compute a target position of the target vessel image, a first feature point of the target vessel, and a second feature point of a branch to which the selected target vessel center line belongs.

The viewing ray vector calculating unit is configured to calculate a viewing ray vector based on the first feature point of the target vessel and the second feature point of the branch to which the selected target vessel center line belongs.

The rotation angle calculating unit is configured to simulate a rotation of the target vessel image at the target position of the target vessel image, and configured to acquire a rotation angle when the viewing ray vector is perpendicular to the screen inward.

The viewing angle adjusting unit is configured to adjust the viewing angle of the display of the target vessel image based on the rotation angle.

In one of the embodiments, the viewing angle adjusting module includes a trajectory information adjusting module 1002, and a depth information adjusting module 1004.

The trajectory information adjusting module 1002 is configured to adjust trajectory information of the corresponding point.

The depth information adjusting module 1004 is configured to adjust the depth information of the corresponding point.

The various modules in the position adjusting device for the three-dimensional target vessel center line above may be implemented in whole or in part by software, hardware, and combinations thereof. The various modules may be embedded in or independent of a processor of a computer device by means of hardware, or may be stored in a memory of the computer device by means of software, so that the processor calls and performs the operations corresponding to the various modules above.

Figure 16:
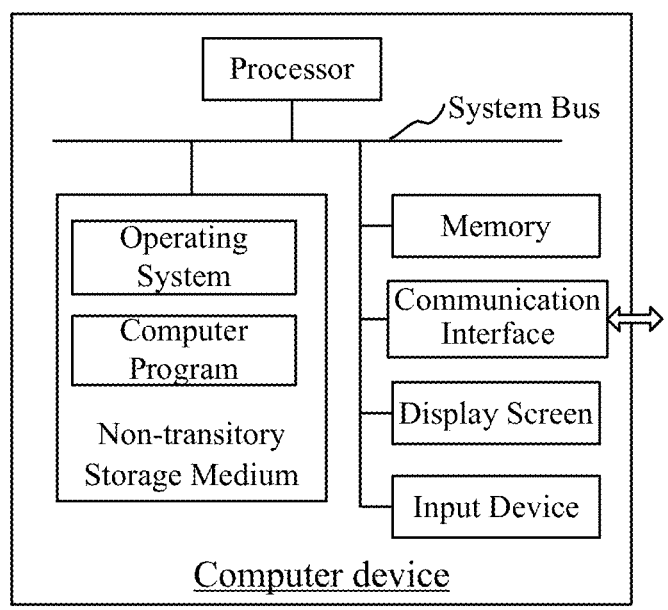
FIG. 16 is a view showing an internal structure of a computer device according to another embodiment of the present disclosure.

In one of the embodiments, a computer device is provided. The computer device may be a terminal, the internal structure of which is shown in FIG. 16. The computer device includes a processor, a memory, a communication interface, a display screen, and an input device which are connected by a system bus. The processor of the computer device is configured to provide computing and control capabilities. The memory of the computer device includes a non-transitory storage medium and a memory. The non-transitory storage medium stores an operating system and a computer program. The memory provides an environment for the operation of an operating system and a computer program in a non-transitory storage medium. The communication interface of the computer device is used for wire or wireless communication with external terminals, and the wireless communication may be implemented by WIFI, mobile cellular network, NFC (near field communication) or other technologies. The computer program, when executed by the processor, performs the vessel displaying method. The display screen of the computer device may be a liquid crystal display screen or an electronic ink display screen, and the input device of the computer device may be a touch layer covered on the display screen, or may be a key, a trackball or a touch pad provided on the housing of the computer device, or may be an external keyboard, a touch pad or a mouse.

It should be understood by those skilled in the art that the structure shown in FIG. 16 is a block diagram showing only part of the structure associated with the solutions of the present application, but not intend to limit the computer device to which the solutions of the present application are applied, and that the particular computer device may include more or less components than those shown in the figure, or may combine with certain components, or may have different component arrangements.

In one of the embodiments, a computer device is provided. The computer device includes a memory having a computer program stored therein, and a processor. The processor, when executing the computer program, performs the steps of: receiving a position adjusting instruction for the target vessel center line; obtaining a corresponding point on the target vessel center line according to the position adjusting instruction for the target vessel center line; extending a view ray in a current viewing-ray direction based on the corresponding point to obtain a front-surface intersection and a rear-surface intersection on the target vessel in the current viewing-ray direction, respectively; and determining depth information of the corresponding point according to the front-surface intersection and the rear-surface intersection.

In one of the embodiments, the extending a view ray in a current viewing-ray direction based on the corresponding point performed by the processor when executing the computer program, includes: acquiring the current viewing-ray direction, and the front-surface intersection and the rear-surface intersection on the target vessel in the current viewing-ray direction; generating a unit vector according to the front-surface intersection and the rear-surface intersection; and extending the viewing ray along the unit vector direction sequentially by at least one unit vector length from the corresponding point.

In one of the embodiments, the processor, when executing the computer program, further performs steps of: acquiring a previous center-line point of the corresponding point on the target vessel center line when the viewing ray extended along the current viewing-ray direction based on the corresponding point does not contact the vessel tissue; and using depth information of the previous center-line point as the depth information of the corresponding point.

In one of the embodiments, the processor, when executing the computer program, further performs steps of: acquiring a preset length when the viewing ray extended along the current viewing-ray direction based on the corresponding point contacts a non-vessel tissue first; acquiring a target point at which the current viewing ray intersects with the non-vessel tissue, and determining whether a length extended based on the target point along the current viewing-ray direction is less than the preset length; when the length extended based on the target point in the current viewing-ray direction is less than the preset length, continuing to extend the viewing ray in the current viewing-ray direction based on the target point, till the viewing ray contacts the vessel tissue to obtain the front-surface intersection and the rear-surface intersection on the target vessel; and calculating the depth information of the corresponding point according to the front-surface intersection and the rear-surface intersection.

In one of the embodiments, the processor, when executing the computer program, further performs steps of: acquiring the previous center-line point of the corresponding point on the vessel center line when the length extended based on the target point in the current viewing-ray direction is greater than or equal to the preset length; using the depth information of the previous center-line point as the depth information of the corresponding point.

In one of the embodiments, before the receiving the position adjusting instruction for the target vessel center line, the processor, when executing the computer program, further performs steps of: receiving a selecting instruction for the target vessel center line through the target vessel image; adjusting a viewing angle of the display of the target vessel image according to the target vessel center line selected based on the selecting instruction for the target vessel center line.

In one of the embodiments, the adjusting the viewing angle of the display of the target vessel image according to the target vessel center line selected based on the selecting instruction for the target vessel center line, performed by the processor when executing the computer program, includes: computing a target position of the target vessel image, a first feature point of the target vessel, and a second feature point of a branch to which the selected target vessel center line belongs; calculating a viewing ray vector based on the first feature point of the target vessel and the second feature point of the branch to which the selected target vessel center line belongs; simulating a rotation of the target vessel image at the target position of the target vessel image, and acquiring a rotation angle when the viewing ray vector is perpendicular to the screen inward; and adjusting the viewing angle of the display of the target vessel image based on the rotation angle.

In one of the embodiments, after the obtaining the corresponding point on the target vessel center line according to the position adjusting instruction for the target vessel center line, the processor, when executing the computer program, further performs adjusting trajectory information of the corresponding point; and after determining the depth information of the corresponding point according to the front-surface intersection and the rear-surface intersection, the processor, when executing the computer program, further performs adjusting the depth information of the corresponding point.

In one of the embodiments, a computer readable storage medium is provided and has a computer program stored thereon. The computer program, when executed by a processor, performs steps of: receiving a position adjusting instruction for the target vessel center line; obtaining a corresponding point on the target vessel center line according to the position adjusting instruction for the target vessel center line; extending a view ray in a current viewing-ray direction based on the corresponding point to obtain a front-surface intersection and a rear-surface intersection on the target vessel in the current viewing-ray direction, respectively; determining depth information of the corresponding point according to the front-surface intersection and the rear-surface intersection.

In one of the embodiments, the extending a view ray in a current viewing-ray direction based on the corresponding point performed by the computer program when executed by the processor, includes: acquiring the current viewing-ray direction, and the front-surface intersection and the rear-surface intersection on the target vessel in the current viewing-ray direction; generating a unit vector according to the front-surface intersection and the rear-surface intersection; and extending the viewing ray along the unit vector direction sequentially by at least one unit vector length from the corresponding point.

In one of the embodiments, the computer program, when executed by the processor, further performs steps of: acquiring a previous center-line point of the corresponding point on the target vessel center line when the viewing ray extended along the current viewing-ray direction based on the corresponding point does not contact the vessel tissue; and using depth information of the previous center-line point as the depth information of the corresponding point.

In one of the embodiments, the computer program, when executed by the processor, further performs steps of: acquiring a preset length when the viewing ray extended along the current viewing-ray direction based on the corresponding point contacts a non-vessel tissue first; acquiring a target point at which the current viewing ray intersects with the non-vessel tissue, and determining whether a length extended based on the target point along the current viewing-ray direction is less than the preset length; when the length extended based on the target point in the current viewing-ray direction is less than the preset length, continuing to extend the viewing ray in the current viewing-ray direction based on the target point, till the viewing ray contacts the vessel tissue to obtain the front-surface intersection and the rear-surface intersection on the target vessel; and calculating the depth information of the corresponding point according to the front-surface intersection and the rear-surface intersection.

In one of the embodiments, the computer program, when executed by the processor, further performs steps of: acquiring the previous center-line point of the corresponding point on the vessel center line, when the length extended based on the target point in the current viewing-ray direction is greater than or equal to the preset length; and using the depth information of the previous center-line point as the depth information of the corresponding point.

In one of the embodiments, before the receiving the position adjusting instruction for the target vessel center line, the program, when executed by the processor, further performs steps of: receiving a selecting instruction for the target vessel center line through the target vessel image; adjusting a viewing angle of the display of the target vessel image according to the target vessel center line selected based on the selecting instruction for the target vessel center line.

In one of the embodiments, the adjusting the viewing angle of the display of the target vessel image according to the target vessel center line selected based on the selecting instruction for the target vessel center line, performed by the computer program when executed by the processor, includes: computing a target position of the target vessel image, a first feature point of the target vessel, and a second feature point of a branch to which the selected target vessel center line belongs; calculating a viewing ray vector based on the first feature point of the target vessel and the second feature point of the branch to which the selected target vessel center line belongs; simulating a rotation of the target vessel image at the target position of the target vessel image, and acquiring a rotation angle when the viewing ray vector is perpendicular to the screen inward; and adjusting the viewing angle of the display of the target vessel image based on the rotation angle.

In one of the embodiments, after the obtaining the corresponding point on the target vessel center line according to the position adjusting instruction for the target vessel center line, the program, when executed by the processor, further performs adjusting trajectory information of the corresponding point; and after determining the depth information of the corresponding point according to the front-surface intersection and the rear-surface intersection, the program, when executed by the processor, further performs adjusting the depth information of the corresponding point.

In one of the embodiments, a computer program product is provided and includes a computer program. The computer program, when executed by a processor, performs steps of: receiving a position adjusting instruction for the target vessel center line; obtaining a corresponding point on the target vessel center line according to the position adjusting instruction for the target vessel center line; extending a view ray in a current viewing-ray direction based on the corresponding point to obtain a front-surface intersection and a rear-surface intersection on the target vessel in the current viewing-ray direction, respectively; and determining depth information of the corresponding point according to the front-surface intersection and the rear-surface intersection.

In one of the embodiments, the extending a view ray in a current viewing-ray direction based on the corresponding point performed by the computer program when executed by the processor, includes: acquiring the current viewing-ray direction, and the front-surface intersection and the rear-surface intersection on the target vessel in the current viewing-ray direction; generating a unit vector according to the front-surface intersection and the rear-surface intersection; and extending the viewing ray along the unit vector direction sequentially by at least one unit vector length from the corresponding point.

In one of the embodiments, the computer program, when executed by the processor, further performs steps of: acquiring a previous center-line point of the corresponding point on the target vessel center line when the viewing ray extended along the current viewing-ray direction based on the corresponding point does not contact the vessel tissue; and using depth information of the previous center-line point as the depth information of the corresponding point.

In one of the embodiments, the computer program, when executed by the processor, further performs steps of: acquiring a preset length when the viewing ray extended along the current viewing-ray direction based on the corresponding point contacts a non-vessel tissue first; acquiring a target point at which the current viewing ray intersects with the non-vessel tissue, and determining whether a length extended based on the target point along the current viewing-ray direction is less than the preset length; when the length extended based on the target point in the current viewing-ray direction is less than the preset length, continuing to extend the viewing ray in the current viewing-ray direction based on the target point, till the viewing ray contacts the vessel tissue to obtain the front-surface intersection and the rear-surface intersection on the target vessel;

and calculating the depth information of the corresponding point according to the front-surface intersection and the rear-surface intersection.

In one of the embodiments, the computer program, when executed by the processor, further performs steps of: acquiring the previous center-line point of the corresponding point on the vessel center line when the length extended based on the target point in the current viewing-ray direction is greater than or equal to the preset length; and using the depth information of the previous center-line point as the depth information of the corresponding point.

In one of the embodiments, before the receiving the position adjusting instruction for the target vessel center line, the program, when executed by the processor, further performs steps of: receiving a selecting instruction for the target vessel center line through the target vessel image; and adjusting a viewing angle of the display of the target vessel image according to the target vessel center line selected based on the selecting instruction for the target vessel center line.

In one of the embodiments, the adjusting the viewing angle of the display of the target vessel image according to the target vessel center line selected based on the selecting instruction for the target vessel center line, performed by the computer program when executed by the processor, includes: computing a target position of the target vessel image, a first feature point of the target vessel, and a second feature point of a branch to which the selected target vessel center line belongs; calculating a viewing ray vector based on the first feature point of the target vessel and the second feature point of the branch to which the selected target vessel center line belongs; simulating a rotation of the target vessel image at the target position of the target vessel image, and acquiring a rotation angle when the viewing ray vector is perpendicular to the screen inward; and adjusting the viewing angle of the display of the target vessel image based on the rotation angle.

In one of the embodiments, after the obtaining the corresponding point on the target vessel center line according to the position adjusting instruction for the target vessel center line, the program, when executed by the processor, further performs adjusting trajectory information of the corresponding point; and after determining the depth information of the corresponding point according to the front-surface intersection and the rear-surface intersection, the program, when executed by the processor, further performs adjusting the depth information of the corresponding point.

A person of ordinary skill in the art should understand that all or part of the processes in the method of the above embodiments may be implemented by means of a computer program instructing relevant hardware. The computer program may be stored in a non-transitory computer readable storage medium. When the computer program is executed, it may include the procedures of the embodiments of the above method. Where, any reference to the memory, the storage, the database or other medium used in the embodiments provided by the present application may include non-transitory memory and transitory memory. The non-transitory memory may include read only memory (ROM), programmable ROM (PROM), electrically programmable ROM (EPROM), electrically erasable programmable ROM (EEPROM), or flash memory. The transitory memory may include random access memory (RAM) or external cache memory. As an illustration but not a limitation, RAM can be in various forms, such as static random access memory (SRAM) or dynamic random access memory (DRAM), synchronous DRAM (SDRAM), double data rate SDRAM (DDRSDRAM), enhanced SDRAM (ESDRAM), synchronous link (Synchlink) DRAM (SLDRAM), memory bus (Rambus) direct RAM (RDRAM), direct memory bus dynamic RAM (DRDRAM), and memory bus dynamic RAM (RDRAM).

The technical features of the above embodiments may be combined arbitrarily. In order to make the description concise, not all possible combinations of the technical features of the above embodiments are described. However, as long as there is no contradiction in the combination of these technical features, any combination should be within the range described in this description.

The above examples are only several embodiments of the present application, and the descriptions thereof are more specific and detailed, but they should not be understood to be a limitation on the scope of the present invention. It should be noted that, for those of ordinary skill in the art, several modifications and improvements may be made without departing from the concept of the present application, and all these modifications and improvements fall within the protection scope of the present application. Therefore, the protection scope of the present application shall be subject to the appended claims.

What is claimed is:

1. A vessel displaying method, comprising:
   acquiring vessel information of a detected object, the vessel information comprising a vessel segment center line and corresponding vessel segment data of each vessel segment;
   receiving an edit instruction;
   editing an initial target vessel segment center line based on the edit instruction, to obtain a final target vessel segment center line;
   constructing a final target vessel segment according to the final target vessel segment center line;
   constructing a target vessel based on the final target vessel segment, and displaying the target vessel;
   receiving a position adjusting instruction for a target vessel center line;
   obtaining a corresponding point on the target vessel center line according to the position adjusting instruction for the target vessel center line;
   extending a view ray in a current viewing-ray direction based on the corresponding point to obtain a front-surface intersection and a rear-surface intersection on the target vessel in the current viewing-ray direction, respectively; and
   determining depth information of the corresponding point according to the front-surface intersection and the rear-surface intersection.

2. The method of claim 1, wherein:
   the receiving the edit instruction comprises receiving a trim instruction, the trim instruction comprising to-be-trimmed region data; and
   the editing the initial target vessel segment center line based on the edit instruction to obtain the final target vessel segment center line, comprises:
      determining an initial target vessel segment based on the trim instruction, and obtaining the initial target vessel segment center line of the initial target vessel segment;
      determining whether each initial center-line point of the initial target vessel segment center line is in the to-be-trimmed region data; and
      determining that the initial center-line point is a target center-line point corresponding to the trim instruction in response to the initial center-line point being in the to-be-trimmed region data, and deleting the target center-line point from the initial target vessel segment center line to obtain the final target vessel segment center line.

3. The method of claim 2, wherein the constructing the final target vessel segment according to the final target vessel segment center line, comprises:
obtaining initial target vessel segment data corresponding to the initial target vessel segment;
deleting initial vessel segment point data corresponding to the to-be-trimmed region data from the initial target vessel segment data to obtain final target vessel segment data; and
constructing the final target vessel segment according to the final target vessel segment data and the final target vessel segment center line.

4. The method of claim 1, wherein:
the receiving the edit instruction, comprises receiving a modification instruction, the modification instruction comprising a vessel segment identification of an initial target vessel segment to be modified and to-be-modified region data; and
the editing the initial target vessel segment center line based on the edit instruction to obtain the final target vessel segment center line, comprises:
obtaining the initial target vessel segment center line of the initial target vessel segment to be modified according to the vessel segment identification;
dividing the initial target vessel segment center line according to the to-be-modified region data, to obtain an initial first center line corresponding to the to-be-modified region data and a second center line without modification; and
modifying a vessel name and/or the vessel segment identification for the initial first center line, to obtain a final first center line.

5. The method of claim 4, wherein the constructing the final target vessel segment according to the final target vessel segment center line, comprises:
obtaining initial target vessel segment data of the initial target vessel segment to be modified according to the vessel segment identification;
extracting vessel segment point data corresponding to the to-be-modified region data from the initial target vessel segment data, to obtain initial first vessel segment data to be modified;
deleting the initial first vessel segment data from the initial target vessel segment data, to obtain second vessel segment data without modification;
modifying the vessel name and/or the vessel segment identification in the initial first vessel segment data, to obtain final first vessel segment data; and
constructing a final first target vessel segment according to the final first center line and the final first vessel segment data, and constructing a second target vessel segment according to the second center line and the second vessel segment data.

6. The method of claim 1, wherein:
the receiving the edit instruction comprises receiving an adding instruction, the adding instruction comprising to-be-added vessel segment data of a vessel segment to be added and a vessel segment identification of an initial target vessel segment; and
the editing the initial target vessel segment center line based on the edit instruction to obtain the final target vessel segment center line, comprises:

obtaining the initial target vessel segment center line and initial target vessel segment data of the initial target vessel segment according to the vessel segment identification of the initial target vessel segment;
generating combined vessel segment data based on the to-be-added vessel segment data and the initial target vessel segment data;
determining a corresponding combined vessel segment center line according to the combined vessel segment data; and
generating the final target vessel segment center line based on the initial target vessel segment center line and the combined vessel segment center line.

7. The method of claim 1, wherein the acquiring the vessel information of the detected object comprises:
acquiring scanned data of the detected object;
dividing the scanned data to obtain original vessel information corresponding to the detected object;
performing a thinning and skeletonization processing on the vessel information, to obtain the vessel segment center line corresponding to each vessel segment; and
determining, based on each vessel segment center line, the vessel segment data of each vessel segment among the original vessel information.

8. The method of claim 1, further comprising:
acquiring vessel segment center lines and corresponding vessel segment data of all non-target vessel segments; and
constructing all the non-target vessel segments based on the vessel segment center lines and the corresponding vessel segment data of the non-target vessel segments.

9. The method of claim 1, wherein the extending the view ray in the current viewing-ray direction based on the corresponding point, comprises:
acquiring the current viewing-ray direction of the corresponding point, and the front-surface intersection and the rear-surface intersection on the target vessel in the current viewing-ray direction;
generating a unit vector according to the front-surface intersection and the rear-surface intersection; and
extending the viewing ray along the unit vector direction sequentially by at least one unit vector length from the corresponding point.

10. The method of claim 1, further comprising:
acquiring a previous center-line point of the corresponding point on the target vessel center line, when the viewing ray extended along the current viewing-ray direction based on the corresponding point does not contact a vessel tissue; and
using depth information of the previous center-line point as the depth information of the corresponding point.

11. The method of claim 1, further comprising:
acquiring a preset length when the viewing ray extended along the current viewing-ray direction based on the corresponding point contacts a non-vessel tissue first;
acquiring a target point at which the current viewing ray intersects with the non-vessel tissue, and determining whether a length extended based on the target point along the current viewing-ray direction is less than the preset length; and
continuing to extend the viewing ray in the current viewing-ray direction based on the target point in response to the length extended based on the target point in the current viewing-ray direction being less than the preset length, till the viewing ray contacts the vessel tissue to obtain the front-surface intersection and the rear-surface intersection on the target vessel, and calculating the depth information of the corresponding point according to the front-surface intersection and the rear-surface intersection.

12. The method of claim 11, further comprising:
acquiring a previous center-line point of the corresponding point on the vessel center line in response to the length extended based on the target point in the current viewing-ray direction being greater than or equal to the preset length; and using the depth information of the previous center-line point as the depth information of the corresponding point.

13. The method of claim 1, wherein, before the receiving the position adjusting instruction for the target vessel center line, the method further comprises:
receiving a selecting instruction for the target vessel center line through a target vessel image; and
adjusting a viewing angle of a display of the target vessel image according to the target vessel center line selected based on the selecting instruction for the target vessel center line.

14. The method of claim 13, wherein the adjusting the viewing angle of the display of the target vessel image according to the target vessel center line selected based on the selecting instruction for the target vessel center line, comprises:
computing a target position of the target vessel image, a first feature point of the target vessel, and a second feature point of a branch to which the selected target vessel center line belongs;
calculating a viewing ray vector based on the first feature point of the target vessel and the second feature point of the branch to which the selected target vessel center line belongs;
simulating a rotation of the target vessel image at the target position of the target vessel image, and acquiring a rotation angle when the viewing ray vector is perpendicular to a screen inward; and
adjusting the viewing angle of the display of the target vessel image based on the rotation angle.

15. The method of claim 1, wherein after the obtaining the corresponding point on the target vessel center line according to the position adjusting instruction for the target vessel center line, the method further comprises adjusting trajectory information of the corresponding point.

16. The method of claim 1, wherein after the determining the depth information of the corresponding point according to the front-surface intersection and the rear-surface intersection, the method further comprises adjusting the depth information of the corresponding point.

17. A computer device, comprising a memory and a processor, wherein the memory has a computer program stored thereon, and the processor, when executing the computer program, performs steps of the method of claim 1.

18. A non-transitory computer readable storage medium, having a computer program stored thereon, wherein the computer program, when executed by a processor, performs steps of the method of claim 1.

* * * * *